(12) United States Patent
Langkopf et al.

(10) Patent No.: US 7,495,002 B2
(45) Date of Patent: Feb. 24, 2009

(54) 3-METHYL-7-BUTINYL-XANTHINES, THE PREPARATION THEREOF AND THEIR USE AS PHARMACEUTICAL COMPOSITIONS

(75) Inventors: Elke Langkopf, Warthausen (DE); Matthias Eckhardt, Biberach (DE); Frank Himmelsbach, Mittelbiberach (DE); Mohammad Tadayyon, Ulm (DE); Leo Thomas, Biberach (DE); Ralf R. H. Lotz, Schemmerhofen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 416 days.

(21) Appl. No.: 11/218,056

(22) Filed: Sep. 1, 2005

(65) Prior Publication Data

US 2006/0079541 A1 Apr. 13, 2006

(30) Foreign Application Priority Data

Sep. 14, 2004 (DE) .................. 10 2004 044 221

(51) Int. Cl.
*C07D 473/06* (2006.01)
*C07D 519/00* (2006.01)
*A61K 31/522* (2006.01)
*A61P 3/10* (2006.01)

(52) U.S. Cl. .............. 514/263.2; 514/263.21; 514/263.22; 514/263.35; 544/268; 544/269; 544/270; 544/272

(58) Field of Classification Search ......... 544/272, 544/268, 269, 270; 514/263.2, 263.21, 263.22, 514/263.35
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,389,642 A | 2/1995 | Dorsch | |
| 5,470,579 A | 11/1995 | Bonte et al. | |
| 5,719,279 A | 2/1998 | Kuefner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano | |
| 6,784,195 B2 | 8/2004 | Hale et al. | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 | 2/2007 | Himmelsbach | |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 2002/0161001 A1 | 10/2002 | Kanstrup | |
| 2002/0169174 A1 | 11/2002 | Chackalamannil et al. | |
| 2002/0198205 A1* | 12/2002 | Himmelsbach et al. | .. 514/234.5 |
| 2003/0105077 A1 | 6/2003 | Kanstrup et al. | |
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |
| 2004/0077645 A1 | 4/2004 | Himmelsbach et al. | |
| 2004/0082570 A1 | 4/2004 | Yoshikawa | |
| 2004/0087587 A1 | 5/2004 | Himmelsbach | |
| 2004/0097510 A1 | 5/2004 | Himmelsbach et al. | |
| 2004/0116328 A1 | 6/2004 | Yoshikawa et al. | |
| 2004/0122228 A1 | 6/2004 | Maier | |
| 2004/0138214 A1 | 7/2004 | Himmelsbach et al. | |

(Continued)

FOREIGN PATENT DOCUMENTS

CA 2136288 A1 5/1995

(Continued)

OTHER PUBLICATIONS

"Patient Information JANUVIA™" <http://www.merck.com/product/usa/pi_circulars/j/januvia/januvia_ppi.pdf> downloaded from the internet Apr. 30, 2008.*

(Continued)

*Primary Examiner*—Mark L Berch
(74) *Attorney, Agent, or Firm*—Michael P. Morris; Mary-Ellen M. Devlin; David L. Kershner

(57) ABSTRACT

The present invention relates to new substituted xanthines of general formula

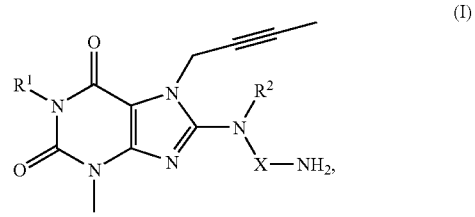

(I)

wherein $R^1$, $R^2$ and X are defined as in the claims, the tautomers, the enantiomers, the diastereomers, the mixtures thereof and the salts thereof, which have valuable pharmacological properties, particularly an inhibiting effect on the activity of the enzyme dipeptidylpeptidase-IV (DPP-IV).

13 Claims, No Drawings

U.S. PATENT DOCUMENTS

| | | |
|---|---|---|
| 2004/0138215 A1 | 7/2004 | Eckhardt |
| 2004/0166125 A1 | 8/2004 | Himmelsbach |
| 2005/0020574 A1 | 1/2005 | Hauel et al. |
| 2005/0026921 A1 | 2/2005 | Eckhardt |
| 2005/0130985 A1 | 6/2005 | Himmelsbach |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0261352 A1 | 11/2005 | Eckhardt |
| 2006/0004074 A1 | 1/2006 | Eckhardt |
| 2006/0058323 A1 | 3/2006 | Eckhardt et al. |
| 2006/0063787 A1 | 3/2006 | Yoshikawa |
| 2006/0094722 A1 | 5/2006 | Yasuda |
| 2006/0142310 A1 | 6/2006 | Pfrengle et al. |
| 2006/0173056 A1 | 8/2006 | Kitajima |
| 2006/0205711 A1 | 9/2006 | Himmelsbach |
| 2006/0247226 A1 | 11/2006 | Himmelsbach |
| 2007/0027168 A1 | 2/2007 | Pfrengle et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0219178 A1 | 9/2007 | Muramoto |
| 2007/0259900 A1 | 11/2007 | Sieger et al. |
| 2007/0281940 A1* | 12/2007 | Dugi et al. ................. 514/248 |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | 37-4895 * | 6/1962 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | 02/068420 A1 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/096806 A1 | 11/2004 |
| WO | 2004/108730 A1 | 12/2004 |
| WO | 2004/050658 A1 | 6/2005 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/048427 A1 | 5/2006 |
| WO | 2006/068163 A1 | 6/2006 |
| WO | 2007/017423 A2 | 2/2007 |

OTHER PUBLICATIONS

U.S. Appl. No. 11/744,701, filed May 4, 2007, Unpublished, Kohlrausch.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Cygankiewicz, Andrzej et al., Investigations into the Piperazine Derivatives of Dimethylxanthine:, ACTA Polon. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors, 2003.

Patani George A. et al.: "Bioisoterism : A Rational Approach in Drug Design", Chemical Reviews, 1996, vol. 96, No. 8, pp. 3147-3176.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

* cited by examiner

3-METHYL-7-BUTINYL-XANTHINES, THE PREPARATION THEREOF AND THEIR USE AS PHARMACEUTICAL COMPOSITIONS

The present invention relates to new substituted xanthines of general formula

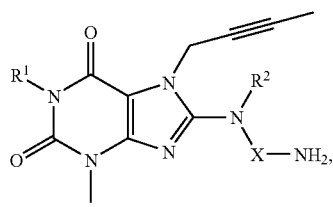
(I)

the tautomers, the enantiomers, the diastereomers, the mixtures thereof and the salts thereof, particularly the physiologically acceptable salts thereof with inorganic or organic acids which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

Related xanthines are described in International Application WO 02/068420.

In the above formula I $R^1$ denotes an arylmethyl or arylethyl group,
a heteroarylmethyl or heteroarylethyl group,
an arylcarbonylmethyl group,
a heteroarylcarbonylmethyl group or
an arylprop-2-enyl or heteroarylprop-2-enyl group, wherein the propenyl chain may be substituted by 1 to 4 fluorine atoms or a cyano, $C_{1-3}$-alkyloxy-carbonyl or nitro group, $R^2$ denotes a $C_{1-4}$-alkyl group, which may be straight-chain or branched, and X denotes a —$CH_2CH_2$ group, which may optionally be substituted by one or two $C_{1-3}$-alkyl groups, which may be identical or different, while by the aryl groups mentioned in the definition of the above groups are meant phenyl or naphthyl groups, which may be mono-, di- or trisubstituted by $R_h$ independently of one another, while the substituents may be identical or different and $R_h$ denotes a fluorine, chlorine, bromine or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, phenyl, morpholinyl, hydroxy, $C_{1-3}$-alkyloxy, difluoromethoxy or trifluoromethoxy group, or two $R_h$ at two adjacent carbon atoms of the aromatic group together form a $C_{3-5}$-alkylene chain, while in the alkylene chain one or two methylene groups may be substituted independently of one another by oxygen atoms or carbonyl groups, and additionally each hydrogen atom may be replaced by a fluorine atom, by the heteroaryl groups mentioned in the definition of the above-mentioned groups are meant a pyrrolyl, furanyl, thienyl, pyridyl, indolyl, benzofuranyl, benzothiophenyl, phenanthridinyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, phenanthridinyl, quinolinyl or isoquinolinyl group, wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxochinoxalinyl, 1,2,3,4-tetrahydro-2,3-dioxo-chinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl, quinolinonyl, imidazoquinolinyl, quinazolinonyl, benzonaphthiridinyl or 3,4-dihydro-3-oxo-2H-benzo[1,4]oxazinyl group, and the above-mentioned heteroaryl groups may be mono- or disubstituted by $R_h$, while the substituents may be identical or different and $R_h$ is as hereinbefore defined, while, unless otherwise stated, the above-mentioned alkyl, alkenyl- and alkynyl groups may be straight-chain or branched, the tautomers, enantiomers, diastereomers, the mixtures thereof, the prodrugs thereof and the salts thereof.

The amino and imino groups mentioned in the definition of the above-mentioned groups may be substituted by a group which can be cleaved in vivo. Such groups are described for example in WO 98/46576.

By a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkoxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-6}$-alkoxycarbonyl or $C_{1-6}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$-CO—O-($R_qCR_r$)-O—CO—, $C_{1-6}$-alkyl- CO—NH-($R_sCR_t$)-O—CO- or $C_{1-6}$-alkyl-CO—O-($R_sCR_t$)-($R_sCR_t$)-O—CO- group, wherein $R_p$ to $R_r$ are as hereinbefore defined, $R_s$ and $R_t$, which may be identical or different, denote hydrogen atoms or $C_{1-3}$-alkyl groups.

Moreover, unless otherwise stated, the saturated alkyl and alkoxy moieties containing more than 2 carbon atoms mentioned in the definitions above also include the branched isomers thereof such as the isopropyl, tert.butyl, isobutyl group, etc.

$R^1$ may denote for example a 2-cyanobenzyl, 3-cyanobenzyl, 2-fluorobenzyl, 3-fluorobenzyl, 3-methoxybenzyl, 4-bromo-2-cyanobenzyl, 3-chloro-2-cyanobenzyl, 2-cyano-4-fluorobenzyl, 2-cyano-5-fluorobenzyl, 2-cyano-6-fluorobenzyl, 4-cyano-3-fluorobenzyl, 4-cyano-3-nitrobenzyl, 3,5-dimethoxybenzyl, 2-cyano-3-methoxybenzyl, 2-cyano-4-methoxybenzyl, 2-cyano-5-methoxybenzyl, 2,6-dicyanobenzyl, 3,4-dicyanobenzyl, 3,5-dicyanobenzyl, 5-cyanofuranylmethyl, oxazolylmethyl, isoxazolylmethyl, 5-methoxycarbonylthienylmethyl, pyridinylmethyl, 3-cyanopyridin-2-ylmethyl, 5-cyanopyridin-2-ylmethyl, 6-cyanopyridin-2-ylmethyl, 4-cyanopyridin-3-ylmethyl, 6-fluoropyridin-2-ylmethyl, pyrimidin-2-yl, 4-methylpyrimidin-2-yl, 4,6-dimethylpyrimidin-2-yl, 3-(2-cyanophenyl)-prop-2-enyl, 3-(2-nitrophenyl)-prop-2-enyl, 3-(pyridin-2-yl)-prop-2-enyl, 3-(pentafluorophenyl)-prop-2-enyl, phenylcarbonylmethyl, 3-methoxyphenylcarbonylmethyl, 1-methyl-benzotriazol-5-ylmethyl, naphth-1-ylmethyl, 4-cyanonaphth-1-ylmethyl, 4-fluoronaphth-1-ylmethyl, 4-bromonaphth-1-ylmethyl, 4-methoxynaphth-1-ylmethyl, quinolin-1-ylmethyl, quinolin-2-ylmethyl, quinolin-6-ylmethyl, quinolin-7-ylmethyl, 3-cyanoquinolin-2-ylmethyl, 4-cyanoquinolin-2-ylmethyl, 8-cyanoquinolin-2-ylmethyl, 8-cyanoquinolin-7-ylmethyl, isoquinolin-1-ylmethyl, 4-cyanoisoquinolin-1-ylmethyl, 1-cyanoisoquinolin-3-ylmethyl, 4-cyanoisoquinolin-3-ylmethyl, 3-methylisoquinolin-1-ylmethyl, quinazolin-2-ylmethyl, 4-methylquinazolin-2-ylmethyl, 4-cyanoquinazolin-2-ylmethyl, 4-aminoquinazolin-2-ylmethyl, 4-morpholin-4-ylquinazolin-2-ylmethyl, [1,5]naphthyridin-2-ylmethyl, [1,5]naphthyridin-3-ylmethyl, [1,8]naphthyridin-2-ylmethyl, phenanthridin-6-ylmethyl, quinoxalin-2-ylmethyl, quinoxalin-6-ylmethyl or 2,3-dimethyl-chinoxalin-6-ylmethyl group.

Preferred compounds of general formula I are those wherein $R^1$ is as hereinbefore defined, $R^2$ denotes a methyl or ethyl group and X denotes a —$CH_2CH_2$ group, which may optionally be substituted by one or two methyl or ethyl groups, while the substituents may be identical or different, the tautomers, enantiomers, diastereomers, the mixtures thereof and the salts thereof.

Particularly preferred are those compounds of general formula I wherein $R^1$ denotes a phenylmethyl, phenylcarbonylmethyl, phenylprop-2-enyl, pyridinylmethyl, pyrimidinylmethyl, naphthylmethyl, quinolinylmethyl, quinolinonylmethyl, imidazoquinolinylmethyl, isoquinolinylmethyl, quinazolinylmethyl, quinazolinonylmethyl, quinoxalinylmethyl, phenanthridinylmethyl, naphthyridinylmethyl, benzonaphthiridinylmethyl, imidazopyridinylmethyl or benzo-triazolylmethyl group which may be substituted in each case by one or two fluorine, chlorine, bromine atoms or one or two cyano, nitro, amino, $C_{1-3}$-alkyl, $C_{1-3}$-alkyloxy, phenyl and morpholinyl groups, while the substituents are identical or different, $R^2$ denotes a methyl group and X denotes a —$CH_2CH_2$ group, which may optionally be substituted by one or two methyl groups, the tautomers, enantiomers, diastereomers, the mixtures thereof and the salts thereof.

Most particularly preferred are those compounds of general formula I wherein $R^1$ denotes a benzyl group substituted by one or two cyano groups or a methoxy and a cyano group or a pyridinylmethyl, pyrimidinylmethyl, quinolinylmethyl, isoquinolinylmethyl, quinazolinylmethyl, quinoxalinylmethyl, naphthyridinylmethyl or naphthylmethyl group, each of which may be substituted by one or two cyano or methyl groups, $R^2$ denotes a methyl group and X denotes a —$CH(CH_3)$-$CH_2$ group, a —$CH_2$—$CH(CH_3)$ group or a —$CH_2$—$C(CH_3)_2$ group, the tautomers, enantiomers, diastereomers, the mixtures thereof and the salts thereof;

but particularly those compounds of general formula I wherein $R^1$ denotes a benzyl group substituted by a cyano group or a pyridinylmethyl, isoquinolinylmethyl, quinazolinylmethyl, quinoxalinylmethyl or naphthyridinylmethyl group, each of which may be substituted by a cyano or methyl group, $R^2$ denotes a methyl group and X denotes a —$CH(CH_3)$-$CH_2$ group, a -$CH_2$—$CH(CH_3)$ group or a —$CH_2$—$C(CH_3)_2$ group, while in each case the carbon atom on the right is linked to the terminal amino group, the tautomers, enantiomers, diastereomers, the mixtures thereof and the salts thereof.

The following preferred compounds are mentioned by way of example:
(a) 1-[(3-methyl-isoquinolin-1-yl)methyl]-3-methyl-7-(2-butyn-1-yl)-8-[(2-amino-ethyl)-methylamino]-xanthine
(b) 1-[(4-methyl-quinazolin-2-yl)methyl]-3-methyl-7-(2-butyn-1-yl)-8-[(2-amino-ethyl)-methylamino]-xanthine
(c) 1-[(3-methyl-isoquinolin-1-yl)methyl]-3-methyl-7-(2-butyn-1-yl)-8-[(2-amino-2-methyl-propyl)-methylamino]-xanthine
(d) 1-[(4-methyl-quinazolin-2-yl)methyl]-3-methyl-7-(2-butyn-1-yl)-8-[(2-amino-2-methyl-propyl)-methylamino]-xanthine
(e) 1-[(3-methyl-isoquinolin-1-yl)methyl]-3-methyl-7-(2-butyn-1-yl)-8-[(S)-(2-amino-propyl)-methylamino]-xanthine
(f) 1-[(3-methyl-isoquinolin-1-yl)methyl]-3-methyl-7-(2-butyn-1-yl)-8-[(R)-(2-amino-propyl)-methylamino]-xanthine
(g) 1-[(4-methyl-quinazolin-2-yl)methyl]-3-methyl-7-(2-butyn-1-yl)-8-[(S)-(2-amino-propyl)-methylamino]-xanthine
(h) 1-[(4-methyl-quinazolin-2-yl)methyl]-3-methyl-7-(2-butyn-1-yl)-8-[(R)-(2-amino-propyl)-methylamino]-xanthine
(i) 1-[(3-methyl-isoquinolin-1-yl)methyl]-3-methyl-7-(2-butyn-1-yl)-8-[(R)-(2-amino-1-methyl-ethyl)-methylamino]-]-xanthine
(j) 1-[(3-methyl-isoquinolin-1-yl)methyl]-3-methyl-7-(2-butyn-1-yl)-8-[(S)-(2-amino-1-methyl-ethyl)-methylamino]-]-xanthine
(k) 1-(2-cyano-benzyl)-3-methyl-7-(2-butyn-1-yl)-8-[(S)-(2-amino-propyl)-methyl-amino]-xanthine
(l) 1-[([1,5]naphthyridin-2-yl)methyl]-3-methyl-7-(2-butyn-1-yl )-8-[(S)-(2-amino-propyl)-methylamino]-xanthine (m) 1-[(quinoxalin-6-yl)methyl]-3-methyl-7-(2-butyn-1-yl)-8-[(S)-(2-amino-propyl)-methylamino]-xanthine (n) 1-[(3-cyano-pyridin-2-yl)methyl]-3-methyl-7-(2-butyn-1-yl)-8-[(S)-(2-amino-propyl)-methylamino]-xanthine (o) 1-[(4-cyano-isoquinolin-3-yl)methyl]-3-methyl-7-(2-butyn-1-yl)-8-[(S)-(2-amino-propyl)-methylamino]-xanthine (p) 1-(2-cyano-benzyl)-3-methyl-7-(2-butyn-1-yl)-8-[(2-amino-2-methyl-propyl)-methylamino]-xanthine (q) 1-[(3-cyano-pyridin-2-yl)methyl]-3-methyl-7-(2-butyn-1-yl)-8-[(2-amino-2-methyl-propyl )-methylamino]-xanthine and the salts thereof.

According to the invention the compounds of general formula I are obtained by methods known per se, for example by the following methods:

a) reacting a compound of general formula

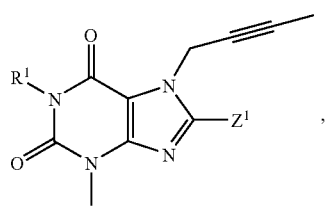

(II)

wherein

R¹ is as hereinbefore defined and

Z¹ denotes a leaving group such as a halogen atom, a substituted hydroxy, mercapto, sulphinyl, sulphonyl or sulphonyloxy group such as e.g. a chlorine, bromine or iodine atom, a methanesulphonyl, trifluoromethanesulphonyloxy or methanesulphonyloxy group, with a compound of general formula

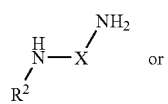

(III)

or

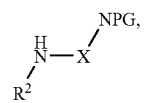

(IV)

wherein R² and X are as hereinbefore defined and NPG denotes a protected or masked amino functionality, derivatives or salts thereof.

Protecting groups for the amino group might be, for example, the formyl, acetyl, trifluoroacetyl, ethoxycarbonyl, tert.-butoxycarbonyl, allyloxycarbonyl, benzyloxy-carbonyl, p-methoxybenzylcarbonyl, benzyl, methoxybenzyl, 2,4-dimethoxybenzyl, phthalyl or tetrachlorophthalyl group. However, the amino group may also be part of a heteroaromatic group, for example, such as e.g. 2,5-dimethylpyrrole and may be released therefrom at a later stage.

The amino function may also be masked in the form of a carboxy group or a derivative thereof, which may be converted into the amino function by so-called Curtius, Schmidt or Hofmann degradation (cf inter alia J. March, Advanced Organic Reactions, Reactions, Mechanisms, and Structure, 4th Edition, John Wiley & Sons, Chichester/New York/Brisbane/Toronto/Singapore, 1992 and literature cited therein).

The reaction is expediently carried out in a solvent such as isopropanol, butanol, tetrahydrofuran, dioxane, dimethylformamide, dimethylsulphoxide, ethyleneglycol monomethyl ether, ethyleneglycol diethyl ether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium- or copper-based catalyst at temperatures between −20 and 180° C., but preferably at temperatures between −10 and 120° C. The reaction may, however, also be carried out without a solvent in an excess of piperidine derivative with conventional heating or in the microwave oven.

b) deprotecting a compound of general formula

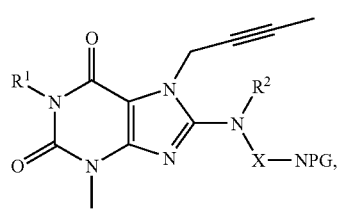

(V)

wherein R¹, R² and X are as hereinbefore defined and NPG denotes a protected or masked amino functionality. Possible protective groups or maskings of the amino function have already been mentioned under a). Preferably the amino group is protected by a tert.-butoxycarbonyl or phthalyl group.

The tert.-butoxycarbonyl group is preferably cleaved by treating with an acid such as trifluoroacetic acid or hydrochloric acid or by treating with bromotrimethylsilane or iodotrimethylsilane, optionally using a solvent such as methylene chloride, ethyl acetate, dioxane, methanol, isopropanol or diethyl ether, at temperatures between 0 and 80° C. The phthalyl group is preferably cleaved in the presence of hydrazine or a primary amine such as methylamine, ethylamine, ethanolamine or n-butylamine in a solvent such as methanol, ethanol, isopropanol, toluene, toluene/water or dioxane, at temperatures between 20 and 120° C.

In the reactions described hereinbefore, any reactive groups present such as amino, alkylamino or imino groups may be protected during the reaction by conventional protecting groups which are cleaved again after the reaction.

For example, protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid, at temperatures between 0 and 100° C., but preferably at ambient temperatures between 20 and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyl or tert. butoxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid, at temperatures between 50 and 120° C. or by treating with sodium hydroxide solution, optionally in the presence of a solvent such as tetrahydrofuran, at temperatures between 0 and 50° C.

A phthalyl group is preferably cleaved in the presence of hydrazine or a primary amine such as methylamine, ethylamine or n-butylamine in a solvent such as methanol, ethanol, ethanolamine, isopropanol, toluene, toluene/water or dioxane at temperatures between 20 and 120° C.

The liberation of an amino function from 2,5-dimethylpyrrole is carried out, for example, with hydroxylamine hydrochloride in the presence of a base such as e.g. triethylamine, in a suitable solvent such as an alcohol, such as e.g. methanol, ethanol, propanol or isopropanol or water or mixtures thereof, at temperatures between 0 and 150° C., but preferably at ambient temperatures between 50 and 110° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained which occur as racemates may be separated by methods known per se (cf. Allinger N. L. and Eliel E. L. in "Topics in Stereochemistry", Vol. 6, Wiley lnterscience, 1971) into their optical enantiomers and compounds of general formula I with at least two asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+)- or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, benzoic acid, fumaric acid, succinic acid, lactic acid, citric acid, tartaric acid or maleic acid.

Moreover, the new compounds of formula (I), if they contain a carboxy group, may if desired be converted into the salts thereof with inorganic or organic bases, particularly for pharmaceutical use into the physiologically acceptable salts thereof. Suitable bases for this include, for example, sodium hydroxide, potassium hydroxide, cyclohexylamine, ethanolamine, diethanolamine and triethanolamine.

The compounds of general formulae II-V used as starting compounds are either known from the literature or may be prepared by methods known from the literature (see Examples I to XI).

As already mentioned hereinbefore, the compounds of general formula I according to the invention and the physiologically acceptable salts thereof have valuable pharmacological properties, particularly an inhibiting effect on the enzyme DPP-IV. The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2", which appeared in Proc. Natl. Acad. Sci. Vol. 90, pp. 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by the addition of 30 µl of solubilised Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example No.) | DPP IV inhibition IC$_{50}$ [nM] |
| --- | --- |
| 1 | 4 |
| 1(1) | 2 |
| 2(1) | 3 |
| 2(4) | 2 |
| 2(5) | 4 |
| 2(9) | 4 |
| 2(10) | 3 |
| 2(11) | 3 |
| 2(12) | 2 |

The compounds prepared according to the invention are well tolerated as no toxic side effects could be detected in rats after the oral administration of 10 mg/kg of the compound of Example 2(4), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, prediabetes, reduced glucose tolerance or changes in the fasting blood sugar, diabetic complications (e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarction. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example.

Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neuro-degenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based thyroid carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Suitable therapeutic agents for such combinations include for example antidiabetic agents such as mefformin, sulphonylureas (e.g. glibenclamide, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), PPAR-gamma/alpha/delta modulators, AMPK activators, ACC1 and ACC2 inhibitors, DGAT-inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, combinations with SGLT2 inhibitors such as T-1095 or KGT-1251 (869682), inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or LXRalpha antagonists, LXRbeta agonists or LXRalpha/beta regulators or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β$_3$-agonists such as SB-418790 or AD-9677 as well as agonists of the 5HT2c receptor, are possible.

It is also possible to combine the compounds with drugs for treating high blood pressure such as e.g. AII antagonists or ACE inhibitors, diuretics, β-blockers, Ca-antagonists, etc., or combinations thereof.

The dosage required to expediently achieve such an effect is, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I

1-[(3-methyl-isoquinolin-1-yl)methyl]-3-methyl-7-(2-butyn-1-yl)-8-bromo-xanthine A mixture of 6.97 g 3-methyl-7-(2-butyn-1-yl)-8-bromo-xanthine, 4.94 g 1-chloromethyl-3-methyl-isoquinoline and 6.64 g potassium carbonate in 56 ml N-methylpyrrolidone is stirred for 3.5 hours at 75° C. For working up it is combined with 80 ml of water. The precipitate formed is suction filtered, washed with water and dried.

Yield: 9.11 g (86% of theory)

$R_f$ value: 0.45 (silica gel, ethyl acetate/petroleum ether=1:1)

The following compounds are obtained analogously to Example I:

(1) 1-[(4-methyl-quinazolin-2-yl)methyl]-3-methyl-7-(2-butyn-1-yl)-8-bromo-xanthine Mass spectrum (ESI$^+$): m/z=453, 455 [M+H]$^+$ (2) 1-(2-cyano-benzyl)-3-methyl-7-(2-butyn-1-yl)-8-bromo-xanthine (carried out in the presence of potassium carbonate in dimethylsulphoxide at 80-90° C.)

$R_f$ value: 0.80 (silica gel, ethyl acetate)

Mass spectrum (ESI$^+$): m/z=412, 414 [M+H]$^+$ (3) 1-[([1,5]naphthyridin-2-yl)methyl]-3-methyl-7-(2-butyn-1-yl)-8-bromo-xanthine (carried out in the presence of potassium carbonate in N,N-dimethylformamide at 80° C.)

$R_f$ value: 0.39 (silica gel, ethyl acetate)

Mass spectrum (ESI$^+$): m/z=439, 441 [M+H]$^+$ (4) 1-[(quinoxalin-6-yl)methyl]-3-methyl-7-(2-butyn-1-yl)-8-bromo-xanthine (carried out in the presence of potassium carbonate in dimethylsulphoxide at 80-85° C.)

$R_f$ value: 0.55 (silica gel, ethyl acetate)

Mass spectrum (ESI$^+$): m/z=439, 441 [M+H]$^+$ (5) 1-[(3-cyano-pyridin-2-yl)methyl]-3-methyl-7-(2-butyn-1-yl)-8-bromo-xanthine $R_f$ value: 0.65 (silica gel, ethyl acetate)

(6) 1-[(4-cyano-isoquinolin-3-yl)methyl]-3-methyl-7-(2-butyn-1-yl)-8-{(S)-[2-(tert.-butoxycarbonylamino)-propyl]-methylamino}-xanthine $R_f$ value: 0.60 (silica gel, ethyl acetate)

Mass spectrum (ESI$^+$): m/z=571 [M+H]$^+$ (7) 1-(4-cyano-benzyl)-3-methyl-7-(2-butyn-1-yl)-8-bromo-xanthine (carried out in the presence of potassium carbonate in N-methylpyrrolidone at 85° C.)

Mass spectrum (ESI$^+$): m/z=412, 414 [M+H]+

(8) 1-(3-cyano-benzyl)-3-methyl-7-(2-butyn-1-yl)-8-bromo-xanthine (carried out in the presence of potassium carbonate in N-methylpyrrolidone at 85° C.)

Mass spectrum (ESI$^+$): m/z=412, 414 [M+H]$^+$

EXAMPLE II

1-[(3-methyl-isopuinolin-1-yl)methyl]-3-methyl-7-(2-butyn-1-yl)-8-{[2-(tert.-butoxycarbonylamino)-2-methyl-propyl]-methylamino}-xanthine 64 mg sodium hydride (60% in mineral oil) are added to 770 mg 1-[(3-methyl-isoquinolin-1-yl)methyl]-3-methyl-7-(2-butyn-1-yl)-8-[2-(tert.-butoxycarbonylamino)-2-methyl-propylamino]-xanthine in 4 ml N,N-dimethylformamide while cooling with ice. After five minutes the ice bath is removed and the reaction mixture is stirred for 15 minutes at ambient temperature. Then 97 μl methyl iodide are added while cooling with an ice bath. After half an hour the reaction is complete. The reaction mixture is combined with some dilute sodium carbonate solution and extracted with ethyl acetate. The combined organic phases are washed with saturated sodium chloride solution, dried over magnesium sulphate and evaporated down. The crude product is triturated with tert.-butylmethylether, suction filtered, washed with a little tert.-butylmethylether and dried.

Yield: 655 mg (83% of theory)

$R_f$ value: 0.60 (silica gel, ethyl acetate/petroleum ether=3:2)

Mass spectrum (ESI$^+$): m/z=574 [M+H]$^+$

The following compounds are obtained analogously to Example II:

(1) 1-[(4-methyl-quinazolin-2-yl)methyl]-3-methyl-7-(2-butyn-1-yl)-8-{[2-(tert.-butoxycarbonylamino)-2-methyl-propyl]-methylamino}-xanthine $R_f$ value: 0.66 (silica gel, ethyl acetate)

Mass spectrum (ESI$^+$): m/z=575 [M+H]$^+$ (2) 1-[(3-methyl-isoquinolin-1-yl)methyl]-3-methyl-7-(2-butyn-1-yl)-8-{(S)-[2-tert.-butoxycarbonylamino)-propyl]-methylamino}-xanthine (carried out with potassium-tert.-butoxide in dimethylsulphoxide)

$R_f$ value: 0.45 (silica gel, methylene chloride/methanol=95:5)

Mass spectrum (ESI$^+$): m/z=560 [M+H]$^+$ (3) 1-[(3-methyl-isoquinolin-1-yl)methyl]-3-methyl-7-(2-butyn-1-yl)-8-{(R)-[2-(tert.-butoxycarbonylamino)-propyl]-methylamino}-xanthine (carried out with potassium-tert.-butoxide in dimethylsulphoxide)

$R_f$ value: 0.70 (silica gel, ethyl acetate)

Mass spectrum (ESI$^+$): m/z=560 [M+H]$^+$ (4) 1-[(4-methyl-quinazolin-2-yl)methyl]-3-methyl-7-(2-butyn-1-yl)-8-{(S)-[2-(tert.-butoxycarbonylamino)-propyl]-methylamino}-xanthine (carried out with potassium-tert.-butoxide in dimethylsulphoxide)

$R_f$ value: 0.40 (silica gel, ethyl acetate)

Mass spectrum (ESI$^+$): m/z=561 [M+H]$^+$ (5) 1-[(4-methyl-quinazolin-2-yl)methyl]-3-methyl-7-(2-butyn-1-yl)-8-{(R)-[2-(tert.-butoxycarbonylamino)-propyl]-methylamino}-xanthine (carried out with potassium-tert.-butoxide in dimethylsulphoxide)

$R_f$ value: 0.30 (silica gel, methylene chloride/methanol=95:5)

Mass spectrum (ESI$^+$): m/z=561 [M+H]$^+$ (6) 1-[(3-methyl-isoquinolin-1-yl)methyl]-3-methyl-7-(2-butyn-1-yl )-8-{(R)-[2-(tert.-butoxycarbonylamino)-1-methyl-ethyl]-methylamino}-xanthine (carried out with potassium-tert.-butoxide in dimethylsulphoxide)

R$_f$ value: 0.55 (silica gel, methylene chloride/methanol=95:5)

Mass spectrum (ESI$^+$): m/z=560 [M+H]$^+$ (7) 1-[(3-methyl-isoquinolin-1-yl)methyl]-3-methyl-7-(2-butyn-1-yl)-8-{(S)-[2-(tert.-butoxycarbonylamino)-1-methyl-ethyl]-methylamino}-xanthine (carried out with potassium-tert.-butoxide in dimethylsulphoxide)

Mass spectrum (ESI$^+$): m/z=560 [M+H]$^+$ (8) 1-(2-cyano-benzyl)-3-methyl-7-(2-butyn-1-yl)-8-{(S)-[2-(tert.-butoxycarbonyl-amino)-propyl]-methylamino}-xanthine (carried out with potassium-tert.-butoxide in dimethylsulphoxide)

R$_f$ value: 0.38 (silica gel, cyclohexane/ethyl acetate=1:1)

Mass spectrum (ESI$^+$): m/z=520 [M+H]$^+$

EXAMPLE III

1-[(3-methyl-isoguinolin-1-yl)methyl]-3-methyl-7-(2-butyn-1-yl)-8-[2-(tert.-butoxycarbonylamino)-2-methyl-propylamino]-xanthine 405 mg di-tert.butyl pyrocarbonate are added to 810 mg 1-[(3-methyl-isoquinolin-1-yl)methyl]-3-methyl-7-(2-butyn-1-yl)-8-(2-amino-2-methyl-propylamino)-xanthine and 0.33 ml diisopropylethylamine in 20 ml of methanol while cooling with ice. The reaction mixture is heated to ambient temperature and stirred overnight. For working up 40 ml ice water are added and the precipitate formed is suction filtered, washed with water, some methanol and tert.-butylmethylether and dried in the desiccator.

Yield: 810 mg (82% of theory)

R$_f$ value: 0.75 (silica gel, methylene chloride/methanol/conc. aqueous ammonia=90:10:1)

Mass spectrum (ESI$^+$): m/z=560 [M+H]$^+$

The following compounds are obtained analogously to Example III:

(1) 1-[(4-methyl-quinazolin-2-yl)methyl]-3-methyl-7-(2-butyn-1-yl)-8-[2-(tert.-butoxycarbonylamino)-2-methyl-propylamino]-xanthine R$_f$ value: 0.54 (silica gel, methylene chloride/methanol/conc. aqueous ammonia=90:10:1)

Mass spectrum (ESI$^+$): m/z=561 [M+H]$^+$ (2) 1-[(3-methyl-isoquinolin-1-yl)methyl]-3-methyl-7-(2-butyn-1-yl)-8-[(S)-2-(tert.-butoxycarbonylamino)-propylamino]-xanthine R$_f$ value: 0.75 (silica gel, ethyl acetate)

Mass spectrum (ESI$^+$): m/z=546 [M+H]$^+$ (3) 1-[(3-methyl-isoquinolin-1-yl)methyl]-3-methyl-7-(2-butyn-1-yl)-8-[(R)-2-(tert.-butoxycarbonylamino)-propylamino]-xanthine Mass spectrum (ESI$^+$): m/z=546 [M+H]$^+$ (4) 1-[(4-methyl-quinazolin-2-yl)methyl]-3-methyl-7-(2-butyn-1-yl)-8-[(S)-2-(tert.-butoxycarbonylamino)-propylamino]-xanthine R$_f$ value: 0.30 (silica gel, ethyl acetate)

Mass spectrum (ESI$^+$): m/z=547 [M+H]$^+$ (5) 1-[(4-methyl-quinazolin-2-yl)methyl]-3-methyl-7-(2-butyn-1-yl)-8-[(R)-2-(tert.-butoxycarbonylamino)-propylamino]-xanthine R$_f$ value: 0.30 (silica gel, ethyl acetate)

Mass spectrum (ESI$^+$): m/z=547 [M+H]$^+$ (6) 1-(2-cyano-benzyl)-3-methyl-7-(2-butyn-1-yl)-8-[(S)-2-(tert.-butoxycarbonylamino)-propylamino]-xanthine R$_f$ value: 0.60 (silica gel, ethyl acetate/petroleum ether=7:3)

Mass spectrum (ESI$^+$): m/z=506 [M+H]$^+$

EXAMPLE IV

1-[(3-methyl-isoguinolin-1-yl)methyl]-3-methyl-7-(2-butyn-1-yl)-8-(2-amino-2-methyl-propylamino)-xanthine A mixture of 1.00 g 1-[(3-methyl-isoquinolin-1-yl)methyl]-3-methyl-7-(2-butyn-1-yl)-8-bromo-xanthine, 0.625 ml 1,2-diamino-2-methylpropane and 500 mg sodium carbonate in 5 ml N-methylpyrrolidone is heated to 200° C. in the microwave for three minutes. The reaction mixture is stirred with water and extracted with ethyl acetate. The combined organic phases are washed with water, dried over magnesium sulphate and evaporated down.

Yield: 830 mg (82% of theory)

R$_f$ value: 0.43 (silica gel, methylene chloride/methanol/conc. aqueous ammonia=90:10:1)

Mass spectrum (ESI$^+$): m/z=460 [M+H]$^+$

The following compounds are obtained analogously to Example IV:

(1) 1-[(4-methyl-quinazolin-2-yl)methyl]-3-methyl-7-(2-butyn-1-yl)-8-(2-amino-2-methyl-propylamino)-xanthine R$_f$ value: 0.39 (silica gel, methylene chloride/methanol/conc. aqueous ammonia=90:10:1)

Mass spectrum (ESI$^+$): m/z=461 [M+H]$^+$ (2) 1-[(3-methyl-isoquinolin-1-yl)methyl]-3-methyl-7-(2-butyn-1-yl)-8-((S)-2-amino-propylamino)-xanthine R$_f$ value: 0.25 (silica gel, methylene chloride/methanol/conc. aqueous ammonia=90:10:0.1)

(3) 1-[(3-methyl-isoquinolin-1-yl)methyl]-3-methyl-7-(2-butyn-1-yl)-8-((R)-2-amino-propylamino)-xanthine Mass spectrum (ESI$^+$): m/z=446 [M+H]$^+$ (4) 1-[(4-methyl-quinazolin-2-yl)methyl]-3-methyl-7-(2-butyn-1-yl)-8-((S)-2-amino-propylamino)-xanthine R$_f$ value: 0.20 (silica gel, methylene chloride/methanol/conc. aqueous ammonia=90:10:0.1)

(5) 1-[(4-methyl-quinazolin-2-yl)methyl]-3-methyl-7-(2-butyn-1-yl)-8-((R)-2-amino-propylamino)-xanthine (6) 1-[(3-methyl-isoquinolin-1-yl)methyl]-3-methyl-7-(2-butyn-1-yl)-8-[(R)-2-(tert.-butoxycarbonylamino)-1-methyl-ethylamino]-xanthine (carried out in the presence of potassium carbonate in dimethylsulphoxide at 80° C.)

R$_f$ value: 0.60 (silica gel, ethyl acetate)

Mass spectrum (ESI$^+$): m/z=546 [M+H]$^+$ (7) 1-[(3-methyl-isoquinolin-1-yl)methyl]-3-methyl-7-(2-butyn-1-yl)-8-[(R)-2-(tert.-butoxycarbonylamino)-1-methyl-ethylamino]-xanthine (carried out in the presence of N-methylmorpholine in dimethylsulphoxide at 80° C.)

R$_f$ value: 0.60 (silica gel, ethyl acetate)

Mass spectrum (ESI$^+$): m/z=546 [M+H]$^{+}$(8) 1-(2-cyano-benzyl)-3-methyl-7-(2-butyn-1-yl)-8-((S)-2-amino-propylamino)-xanthine (carried out in the presence of potassium carbonate in N-methylpyrrolidone at 120° C.)

R$_f$ value: 0.25 (silica gel, methylene chloride/methanol/conc. aqueous ammonia=90:10:0.1)

(9) 1-[([1,5]naphthyridin-2-yl)methyl]-3-methyl-7-(2-butyn-1-yl)-8-{(S)-[2-(tert.-butoxycarbonylamino)-propyl]-methylamino}-xanthine (carried out in the presence of potassium carbonate in dimethylsulphoxide at 1 10° C.)

Mass spectrum (ESI$^+$): m/z=547 [M+H]$^+$

(10) 1-[(quinoxalin-6-yl)methyl]-3-methyl-7-(2-butyn-1-yl)-8-{(S)-[2-(tert.-butoxycarbonylamino)-propyl]-methylamino}-xanthine (carried out in the presence of potassium carbonate in dimethylsulphoxide at 110° C.)

$R_f$ value: 0.55 (silica gel, ethyl acetate)

Mass spectrum (ESI$^+$): m/z=547 [M+H]$^+$

(11) 1-[(3-cyano-pyridin-2-yl)methyl]-3-methyl-7-(2-butyn-1-yl )-8-{(S)-[2-(tert.-butoxycarbonylamino)-propyl]-methylamino}-xanthine (carried out in the presence of potassium carbonate in dimethylsulphoxide at 110° C.)

$R_f$ value: 0.65 (silica gel, ethyl acetate)

Mass spectrum (ESI$^+$): m/z=521 [M+H]$^+$

(12) 3-methyl-7-(2-butyn-1-yl)-8-{(S)-[2-(tert.-butoxycarbonylamino)-propyl]-methylamino}-xanthine (carried out in the presence of potassium carbonate in dimethylsulphoxide at 120° C.)

$R_f$ value: 0.50 (silica gel, ethyl acetate) (13) 1-(2-cyano-benzyl)-3-methyl-7-(2-butyn-1-yl)-8-{[2-(tert.-butoxycarbonylamino)-2-methyl-propyl]-methylamino}-xanthine (carried out in the presence of potassium carbonate in N-methylpyrrolidone at 85° C.)

$R_f$ value: 0.70 (silica gel, methylene chloride/methanol=4:1)

Mass spectrum (ESI$^+$): m/z=534 [M+H]$^+$

(14) 1-[(3-cyano-pyridin-2-yl)methyl]-3-methyl-7-(2-butyn-1-yl)-8-{[2-(tert.-butoxycarbonylamino)-2-methyl-propyl]-methylamino}-xanthine (carried out in the presence of potassium carbonate in N-methylpyrrolidone at 85° C.)

$R_f$ value: 0.30 (silica gel, methylene chloride/methanol=4:1)

Mass spectrum (ESI$^+$): m/z=535 [M+H]$^+$

(15) 1-(4-cyano-benzyl )-3-methyl-7-(2-butyn-1-yl)-8-{[2-(tert.-butoxycarbonylamino)-2-methyl-propyl]-methylamino}-xanthine (carried out in the presence of potassium carbonate in N-methylpyrrolidone at 85° C.)

$R_f$ value: 0.80 (silica gel, methylene chloride/methanol=9:1)

Mass spectrum (ESI$^+$): m/z=534 [M+H]$^+$

(16) 1-(3-cyano-benzyl)-3-methyl-7-(2-butyn-1-yl)-8-{[2-(tert.-butoxycarbonylamino)-2-methyl-propyl]-methylamino}-xanthine (carried out in the presence of potassium carbonate in N-methylpyrrolidone at 85° C.)

$R_f$ value: 0.85 (silica gel, methylene chloride/methanol=9:1)

Mass spectrum (ESI$^+$): m/z=534 [M+H]$^+$

EXAMPLE V tert.butyl ((S)-1-methyl-2-methylamino-ethyl)-carbamate 6.00 ml methylamine solution (2 M in tetrahydrofuran) are added to 1.73 g tert.butyl ((S)-1-methyl-2-oxoethyl)-carbamate in 20 ml benzene with stirring at ambient temperature. Then 2.50 g anhydrous sodium sulphate are added and the reaction mixture is stirred overnight at ambient temperature. The sodium sulphate is suction filtered and washed again with benzene. The filtrate is evaporated down, taken up in 20 ml of methanol and combined with 397 mg sodium cyanoborohydride with stirring at ambient temperature. After 2.5 hours the reaction mixture is acidified by dropwise addition of approx. 20 ml 2 N citric acid and extracted with tert.-butylmethyl-ether. The aqueous phase is made alkaline with 10 M sodium hydroxide solution and extracted with a methylene chloride/methanol mixture. The combined organic phases are dried over magnesium sulphate and evaporated down.

Yield: 1.06 g (56% of theory)

Mass spectrum (ESI$^+$): m/z=189 [M+H]$^+$

EXAMPLE VI 3-bromomethyl-4-cyano-isoquinoline 39 mg azo-isobutyronitrile are added to a boiling mixture of 400 mg 3-methyl-4-cyano-isoquinoline and 440 mg N-bromosuccinimide in 30 ml carbon tetrachloride. The reaction mixture is refluxed for two hours. After cooling to ambient temperature the precipitate formed is suction filtered and washed with carbon tetrachloride. The filtrate is evaporated down and chromatographed through a silica gel column with methylene chloride as eluant.

Yield: 350 mg (60% of theory)

$R_f$ value: 0.40 (silica gel, petroleum ether/ethyl acetate=7:3)

Mass spectrum (ESI$^+$): m/z=247, 249 [M+H]$^+$

EXAMPLE VII 3-methyl-4-cyano-isoguinolin

A mixture of 3.90 g 3-methyl-4-bromo-isoquinoline, 1.47 g zinc cyanide and 2.03 g tetrakis(triphenylphosphine)palladium in 70 ml N-methylpyrrolidone is stirred for 27 hours under an argon atmosphere at 105° C. After cooling to ambient temperature the reaction mixture is combined with 200 ml cyclohexane and stirred with 150 ml of conc. ammonia while cooling with ice. The aqueous phase is separated off and extracted with cyclohexane. The combined organic phases are washed with conc. ammonia and saturated sodium chloride solution, dried over magnesium sulphate and evaporated down. The crude product is purified through a silica gel column with petroleum ether/ethyl acetate (8:2) as eluant.

Yield: 1.90 g (64% of theory)

$R_f$ value: 0.30 (silica gel, petroleum ether/ethyl acetate=7:3)

Mass spectrum (ESI$^+$): m/z=169 [M+H]$^+$

EXAMPLE VIII tert.butyl (1,-dimethyl-2-methylamino-ethyl)-carbamate 22.81 g tert.butyl [2-(benzyl-methyl-amino)-1,1-dimethyl-ethyl]-carbamate in 200 ml of ethanol are hydrogenated in the presence of 2.30 g palladium on activated charcoal (10%) for three hours at ambient temperature and at a partial hydrogen pressure of 68 psi. Then the catalyst is filtered off and the filtrate is evaporated down, leaving a colourless oil.

Yield: 14.38 g (91% of theory)

$R_f$ value: 0.55 (silica gel, cyclohexane/ethyl acetate=2:1)

Mass spectrum (ESI$^+$): m/z=203 [M+H]$^+$

EXAMPLE IX tert.butyl [2-(benzyl-methyl-amino)-1.1-dimethyl-ethyl]-carbamate

A mixture of 34.41 g N$^1$-benzyl-N$^1$,2-dimethyl-propane-1,2-diamine in 280 ml of ethanol, 25.20 ml triethylamine and 39.20 g di-tert.Butyn pyrocarbonate is stirred for two hours at ambient temperature. Then the solvent is distilled off and the flask residue is purified by chromatography through silica gel with cyclohexane/ethyl acetate (100:0 to 66:34) as eluant.

Yield: 22.81 g (44% of theory)

$R_f$ value: 0.80 (silica gel, cyclohexane/ethyl acetate=2:1)

Mass spectrum (ESI$^+$): m/z=293 [M+H]$^+$

EXAMPLE X $N^1$-benzyl-$N^1$,2-dimethyl-propane-1,2-diamine

Analogously to the procedure laid down by K. Taniguchi et al., Chem. Pharm. Bull. 1995, 43, 71-77, 39.78 g N-methyl-N-(2-methyl-2-nitro-propyl)benzylamine are hydrogenated in 280 ml of ethanol in the presence of 7.20 g Raney nickel for three hours at ambient temperature under a partial hydrogen pressure of 53 psi. Then the catalyst is filtered off and the filtrate is further reacted directly (see Example IX).

$R_f$ value: 0.20 (silica gel, cyclohexane/ethyl acetate=2:1)

EXAMPLE XI

N-methyl-N-(2-methyl-2-nitro-proryl)benzylamine

Prepared from 2-nitropropane, N-methylbenzylamine and 37% formaldehyde solution in the presence of sodium hydroxide solution in dioxane analogously to the procedure laid down by K. Taniguchi et al., Chem. Pharm. Bull. 1995, 43, 71-77.

$R_f$ value: 0.85 (silica gel, cyclohexane/ethyl acetate=2:1)

Mass spectrum (ESI$^+$): m/z=223 [M+H]$^+$

Preparation of the end compounds:

EXAMPLE 1

1-[(3-methyl-isoguinolin-1-yl)methyl]-3-methyl-7-(2-butyn-1-yl)-8-[(2-amino-ethyl)-methylaminol]-xanthine

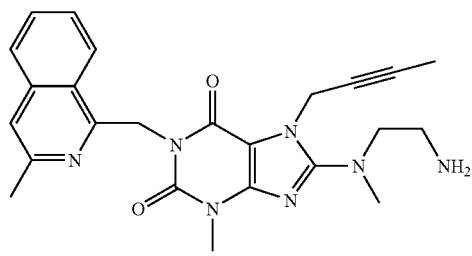

A mixture of 250 mg 1-[(3-methyl-isoquinolin-1-yl)methyl]-3-methyl-7-(2-butyn-1-yl)-8-bromo-xanthine, 0.30 ml N-methyl-ethylenediamine and 75 mg sodium carbonate in 3 ml dimethylsulphoxide is stirred for three hours at 70° C. For working up it is combined with water and extracted with methylene chloride. The combined extracts are dried over magnesium sulphate and evaporated down. The flask residue is chromatographed through a silica gel column with methylene chloride/methanol (10:1 to 2:1) as eluant. 75 mg of the title product and 86 mg of the isomeric product 1-[(3-methyl-isoquinolin-1-yl)methyl]-3-methyl-7-(2-butyn-1-yl)-8-(2-methylamino-ethylamino)-xanthine are obtained.

Yield: 75 mg (30% of theory)

Mass spectrum (ESI$^+$): m/z=447 [M+H]$^+$

The following compounds are obtained analogously to Example 1:

(1) 1-[(4-methyl-quinazolin-2-yl)methyl]-3-methyl-7-(2-butyn-1-yl)-8-[(2-amino-ethyl)-methylamino]-xanthine

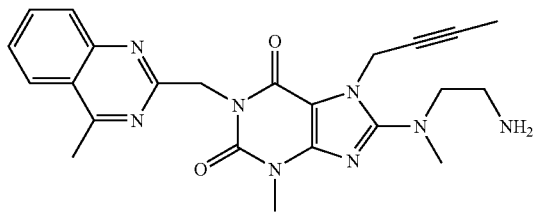

Mass spectrum (ESI$^+$): m/z=447 [M+H]$^+$

EXAMPLE 2

1-[(3-methyl-isoguinolin-1-yl)methyl]-3-methyl-7-(2-butyn-1-yl)-8-[(2-amino-2-methyl-propyl)-methylamino]-xanthine

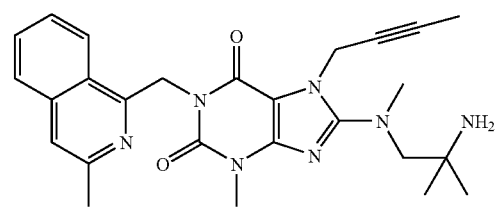

A solution of 610 mg 1-[(3-methyl-isoquinolin-1-yl)methyl]-3-methyl-7-(2-butyn-1-yl)-8-{[2-(tert.-butoxycarbonylamino)-2-methyl-propyl]-methylamino}-xanthine in 10 ml methylene chloride is combined with 2.20 ml isopropanolic hydrochloric acid [5-6 M] and stirred overnight at ambient temperature. The reaction mixture is diluted with methylene chloride and extracted with water. The combined aqueous phases are made alkaline with saturated sodium hydrogen carbonate solution and extracted with methylene chloride. The combined organic phases are dried over magnesium sulphate and evaporated down. The crude product is stirred with tert.-butyl-methyl-ether, suction filtered, washed with a little tert.-butylmethylether and dried in the drying pistol at 60° C.

Yield: 440 mg (87% of theory)

$R_f$ value: 0.46 (silica gel, methylene chloride/methanol/conc. aqueous ammonia=90:10:1)

Mass spectrum (ESI$^+$): m/z=474 [M+H]$^+$

The following compounds are obtained analogously to Example 2:

(1) 1-[(4-methyl-quinazolin-2-yl)methyl]-3-methyl-7-(2-butyn-1-yl)-8-[(2-amino-2-methyl-propyl)-methylamino]-xanthine

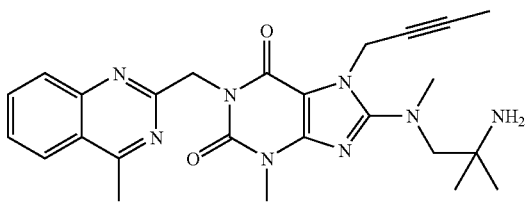

$R_f$ value: 0.57 (silica gel, methylene chloride/methanol/conc. aqueous ammonia=90:10:1)

Mass spectrum (ESI$^+$): m/z=475 [M+H]$^+$ (2) 1-[(3-methyl-isoquinolin-1-yl)methyl]-3-methyl-7-(2-butyn-1-yl)-8-[(S)-(2-amino-propyl)-methylamino]-xanthine

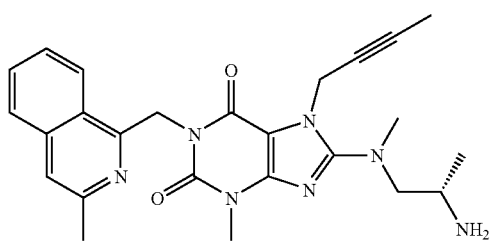

$R_f$ value: 0.45 (silica gel, methylene chloride/methanol/conc. aqueous ammonia=90:10:0.1)

Mass spectrum (ESI$^+$): m/z=460 [M+H]$^+$ (3) 1-[(3-methyl-isoquinolin-1-yl)methyl]-3-methyl-7-(2-butyn-1-yl)-8-[(R)-(2-amino-propyl)-methylamino]-xanthine

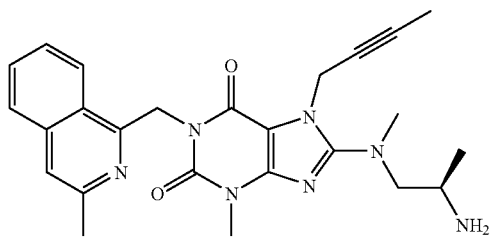

Mass spectrum (ESI$^+$): m/z=460 [M+H]$^+$ (4) 1-[(4-methyl-quinazolin-2-yl)methyl]-3-methyl-7-(2-butyn-1-yl)-8-[(S)-(2-amino-propyl)-methylamino]-xanthine

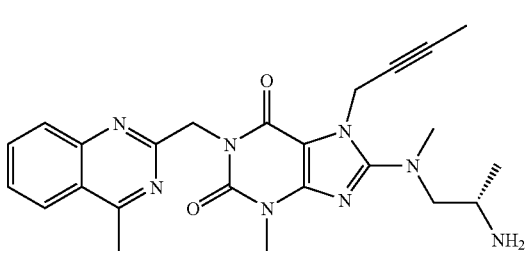

$R_f$ value: 0.40 (silica gel, methylene chloride/methanol/conc. aqueous ammonia=90:10:0.1)

Mass spectrum (ESI$^+$): m/z=461 [M+H]$^+$ (5) 1-[(4-methyl-quinazolin-2-yl)methyl]-3-methyl-7-(2-butyn-1-yl)-8-[(R)-(2-amino-propyl)-methylamino]-xanthine

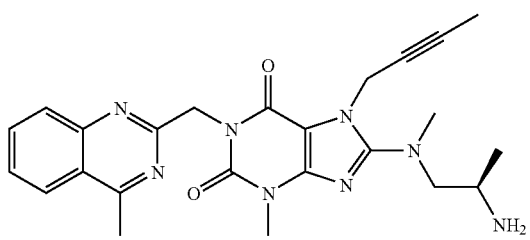

(BOC cleaving carried out with trifluoroacetic acid in methylene chloride)

$R_f$ value: 0.40 (silica gel, methylene chloride/methanol/conc. aqueous ammonia=90:10:0.1)

Mass spectrum (ESI$^+$): m/z=461 [M+H]$^+$ (6) 1-[(3-methyl-isoquinolin-1-yl)methyl]-3-methyl-7-(2-butyn-1-yl)-8-[(R)-(2-amino-1-methyl-ethyl)-methylamino]-]-xanthine

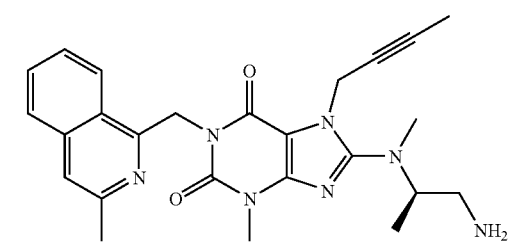

(BOC cleaving carried out with trifluoroacetic acid in methylene chloride)

$R_f$ value: 0.40 (silica gel, methylene chloride/methanol/conc. aqueous ammonia=90:10:0.1)

Mass spectrum (ESI$^+$): m/z=460 [M+H]$^+$ (7) 1-[(3-methyl-isoquinolin-1-yl)methyl]-3-methyl-7-(2-butyn-1-yl)-8-[(S)-(2-amino-1-methyl-ethyl)-methylamino]-]-xanthine

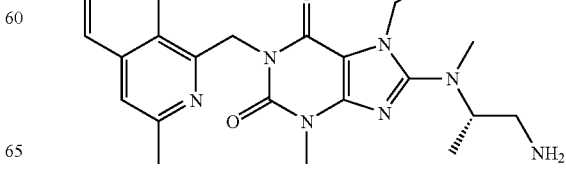

(BOC cleaving carried out with trifluoroacetic acid in methylene chloride)

Mass spectrum (ESI⁺): m/z=460 [M+H]⁺

(8) 1-(2-cyano-benzyl)-3-methyl-7-(2-butyn-1-yl)-8-[(S)-(2-amino-propyl)-methyl-amino]-xanthine

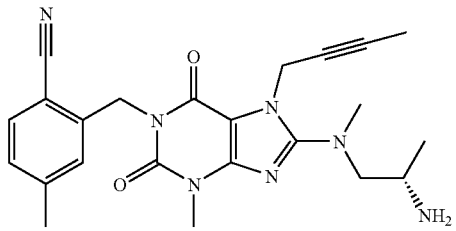

(BOC cleaving carried out with trifluoroacetic acid in methylene chloride)

$R_f$ value: 0.50 (silica gel, methylene chloride/methanol/conc. aqueous ammonia=90:10:0.1)

Mass spectrum (ESI⁺): m/z=420 [M+H]⁺

(9) 1-[([1,5]naphthyridin-2-yl)methyl]-3-methyl-7-(2-butyn-1-yl)-8-[(S)-(2-amino-propyl)-methylamino]-xanthine

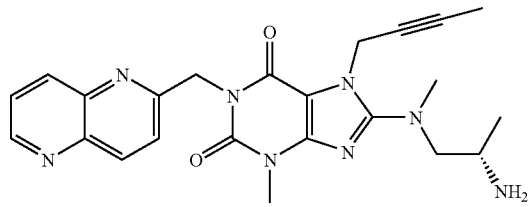

$R_f$ value: 0.47 (silica gel, methylene chloride/methanol/conc. aqueous ammonia=90:10:1)

Mass spectrum (ESI⁺): m/z=447 [M+H]⁺

(10) 1-[(quinoxalin-6-yl)methyl]-3-methyl-7-(2-butyn-1-yl)-8-[(S)-(2-amino-propyl)-methylamino]-xanthine

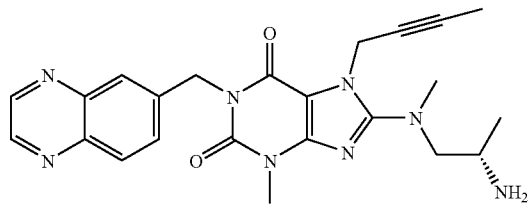

$R_f$ value: 0.50 (silica gel, methylene chloride/methanol/conc. aqueous ammonia=90:10:1)

Mass spectrum (ESI⁺): m/z=447 [M+H]⁺

(11) 1-[(3-cyano-pyridin-2-yl)methyl]-3-methyl-7-(2-butyn-1-yl)-8-[(S)-(2-amino-propyl)-methylamino]-xanthine

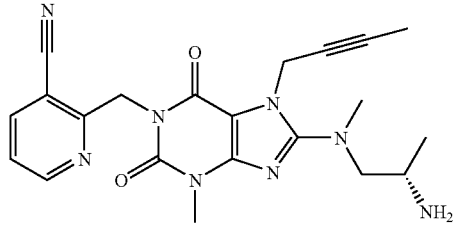

$R_f$ value: 0.55 (silica gel, methylene chloride/methanol/conc. aqueous ammonia=90:10:0.1)

Mass spectrum (ESI⁺): m/z=421 [M+H]⁺

(12) 1-[(4-cyano-isoquinolin-3-yl)methyl]-3-methyl-7-(2-butyn-1-yl)-8-[(S)-(2-amino-propyl)-methylamino]-xanthine

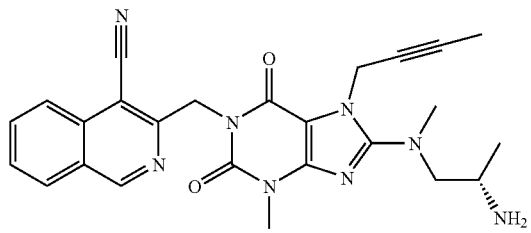

(BOC cleaving carried out with trifluoroacetic acid in methylene chloride)

$R_f$ value: 0.45 (silica gel, methylene chloride/methanol/conc. aqueous ammonia=90:10:0.1)

Mass spectrum (ESI⁺): m/z=471 [M+H]⁺

(13) 1-(2-cyano-benzyl)-3-methyl-7-(2-butyn-1-yl)-8-[(2-amino-2-methyl-propyl)-methylamino]-xanthine

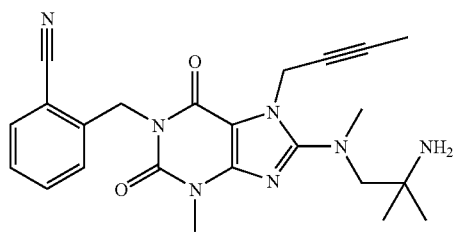

(BOC cleaving carried out with trifluoroacetic acid in methylene chloride)

Mass spectrum (ESI⁺): m/z=434 [M+H]⁺

$R_f$ value: 0.40 (Reversed phase ready-made TLC plate (E. Merck), acetonitrile/water/trifluoroacetic acid=50:50:1)

(14) 1-[(3-cyano-pyridin-2-yl)methyl]-3-methyl-7-(2-butyn-1-yl)-8-[(2-amino-2-methyl-propyl)-methylamino]-xanthine

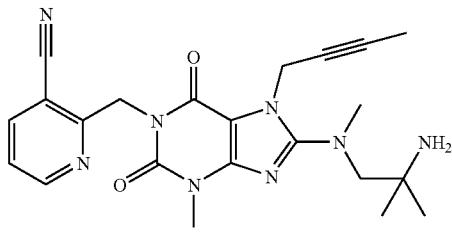

(BOC cleaving carried out with trifluoroacetic acid in methylene chloride)

Mass spectrum (ESI+): m/z=435 [M+H]+

$R_f$ value: 0.50 (Reversed phase ready-made TLC plate (E. Merck), acetonitrile/water/trifluoroacetic acid=50:50:1)

(15) 1-(4-cyano-benzyl)-3-methyl-7-(2-butyn-1-yl)-8-[(2-amino-2-methyl-propyl)-methylamino]-xanthine

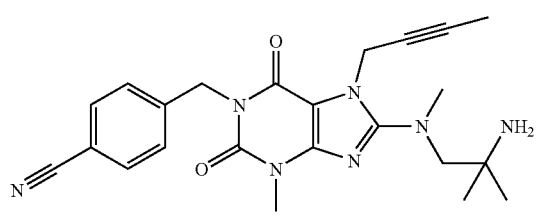

(BOC cleaving carried out with trifluoroacetic acid in methylene chloride)

Mass spectrum (ESI+): m/z=434 [M+H]+

$R_f$ value: 0.40 (Reversed phase ready-made TLC plate (E. Merck), acetonitrile/water/trifluoroacetic acid=50:50:1)

(16) 1-(3-cyano-benzyl)-3-methyl-7-(2-butyn-1-yl)-8-[(2-amino-2-methyl-propyl)-methylamino]-xanthine

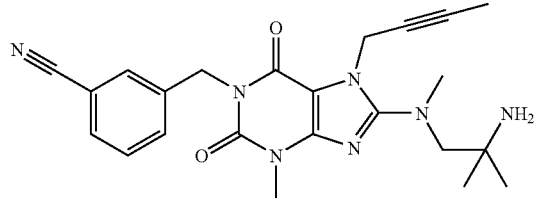

(BOC cleaving carried out with trifluoroacetic acid in methylene chloride)

Mass spectrum (ESI+): m/z=434 [M+H]+

The following compounds may also be obtained analogously to the foregoing Examples and other methods known from the literature:

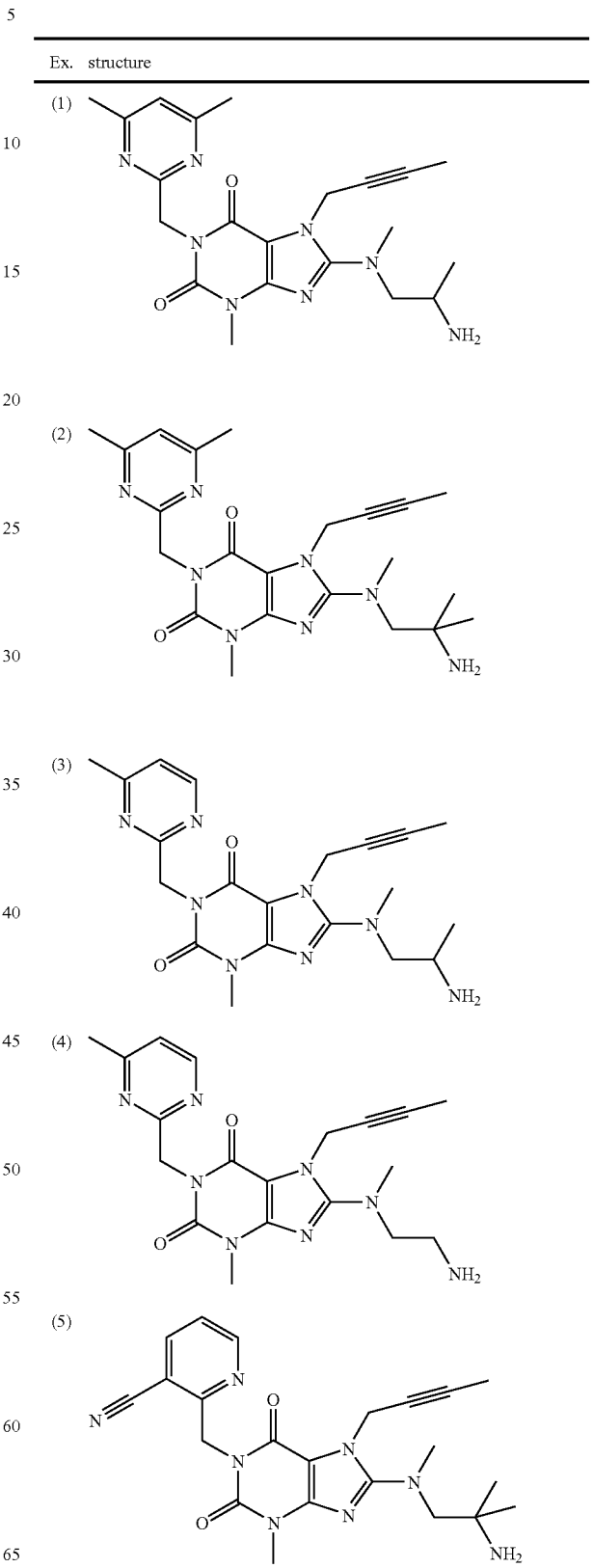

| Ex. | structure |
| --- | --- |
| (1) | 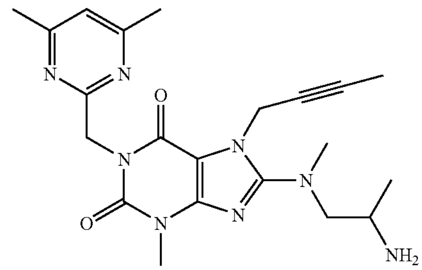 |
| (2) | 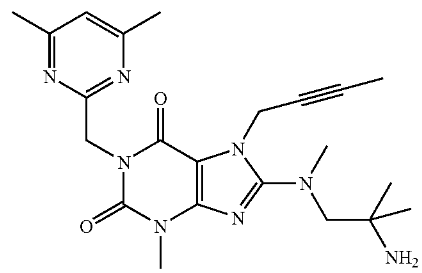 |
| (3) | 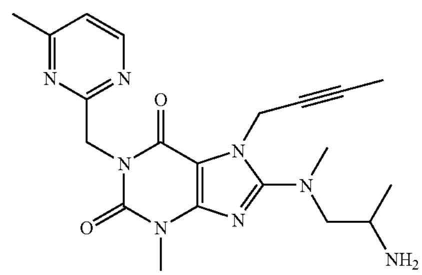 |
| (4) | 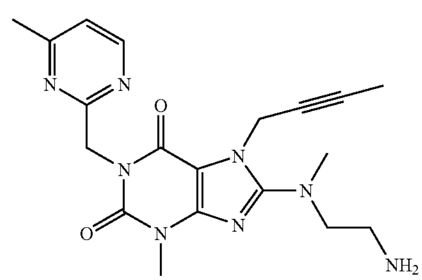 |
| (5) | 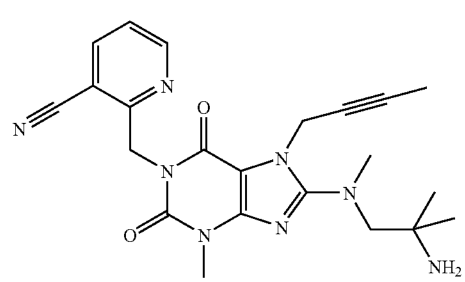 |

| Ex. | structure |
|---|---|
| (6) | 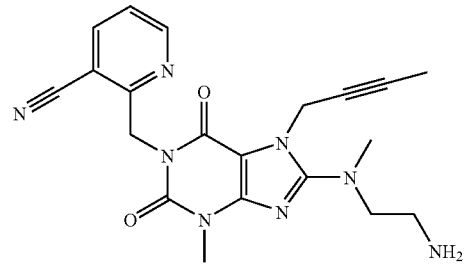 |
| (7) | 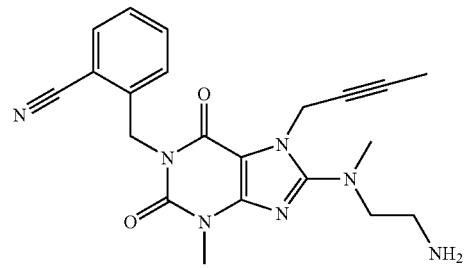 |
| (8) | 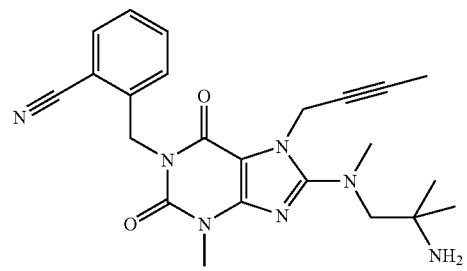 |
| (9) | 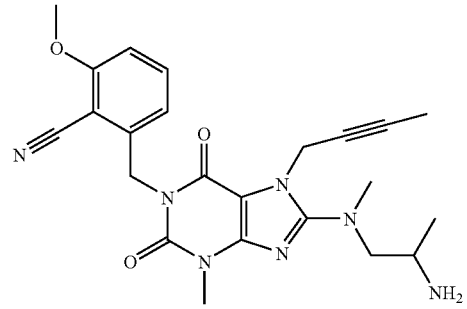 |
| (10) | 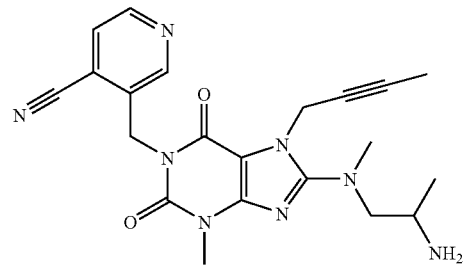 |
| Ex. | structure |
|---|---|
| (11) | 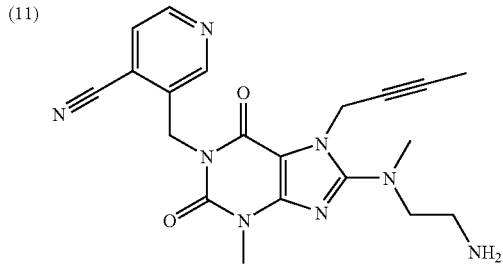 |
| (12) | 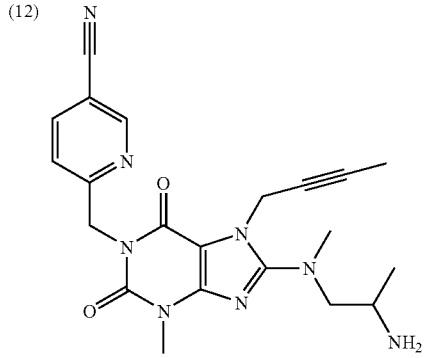 |
| (13) | 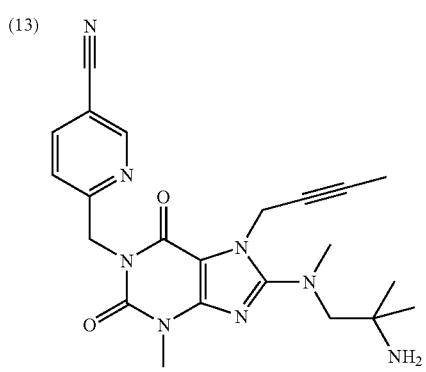 |
| (14) | 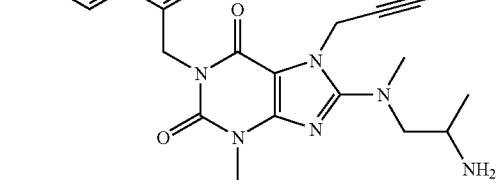 |

-continued
| Ex. | structure |
|---|---|
| (15) | 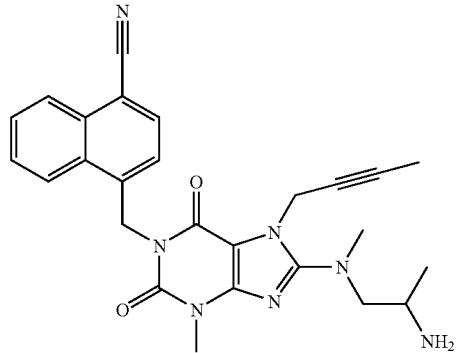 |
| (16) | 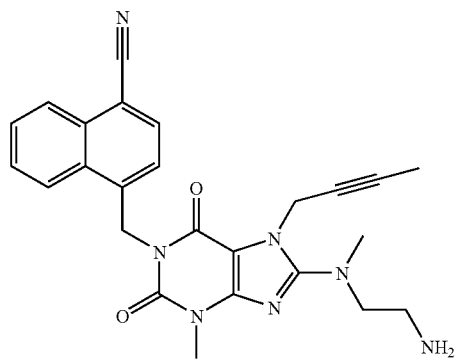 |
| (17) | 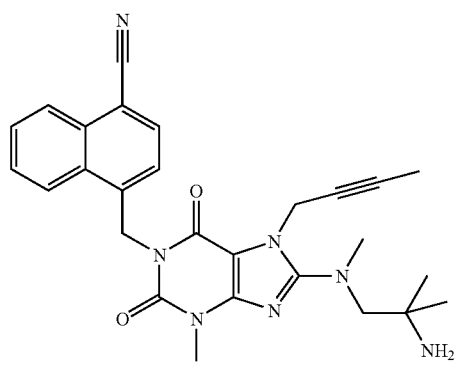 |
| (18) | 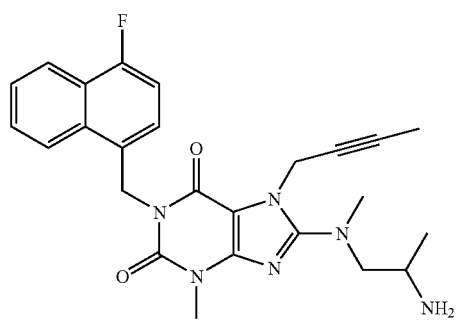 |
-continued
| Ex. | structure |
|---|---|
| (19) | 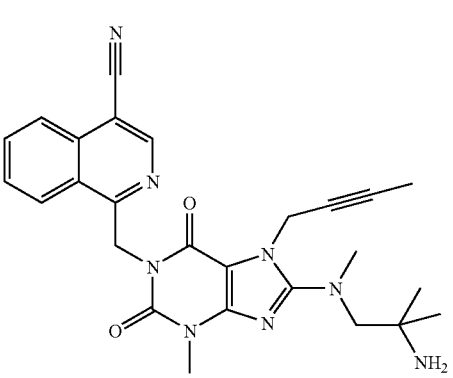 |
| (20) | 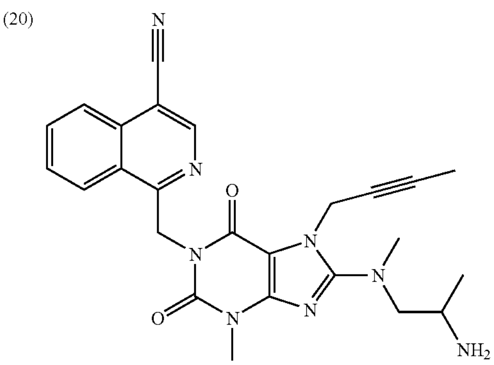 |
| (21) | 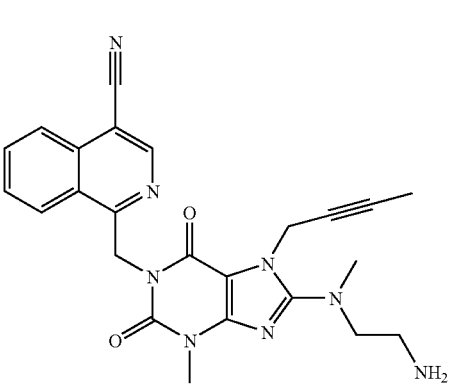 |
| (22) | 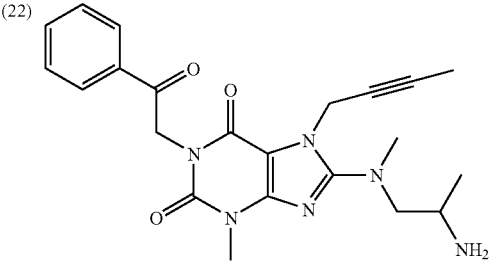 |

-continued
| Ex. | structure |
|---|---|
| (23) | 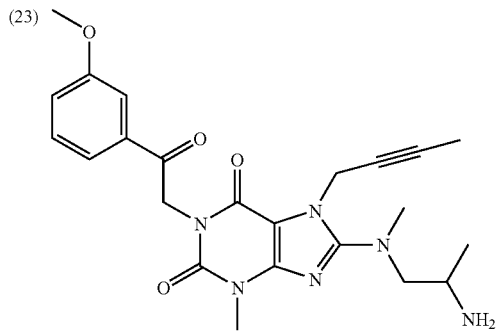 |
| (24) | 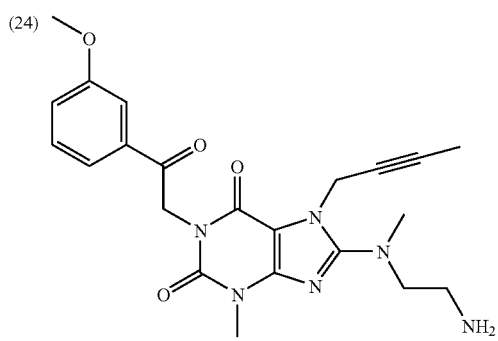 |
| (25) | 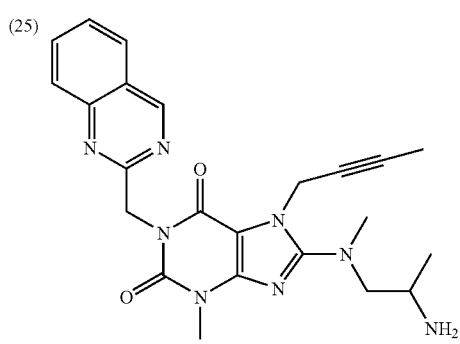 |
| (26) | 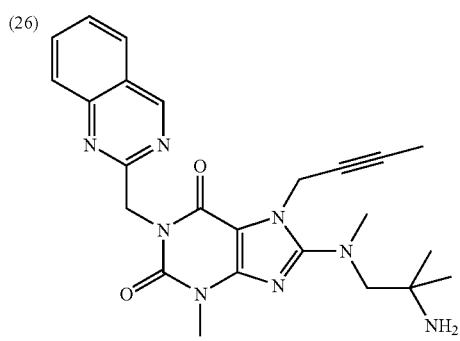 |
| (27) | 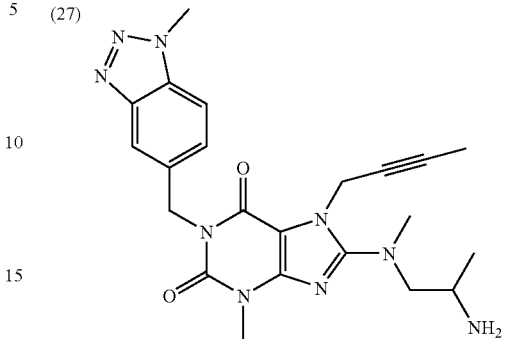 |
| (28) | 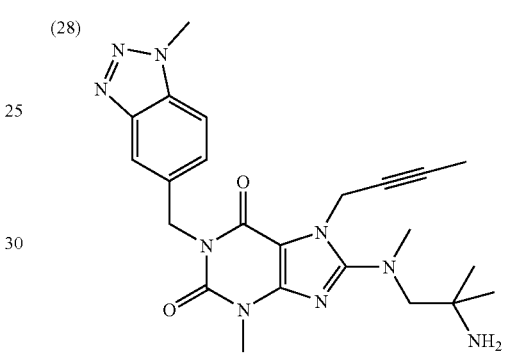 |
| (29) | 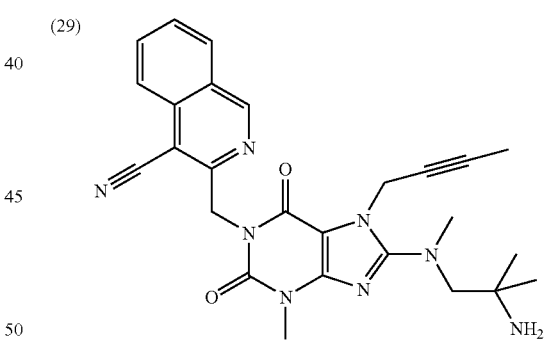 |
| (30) | 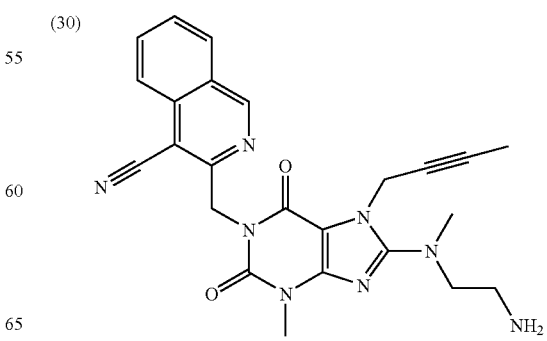 |

-continued
| Ex. | structure |
|---|---|
| (31) | 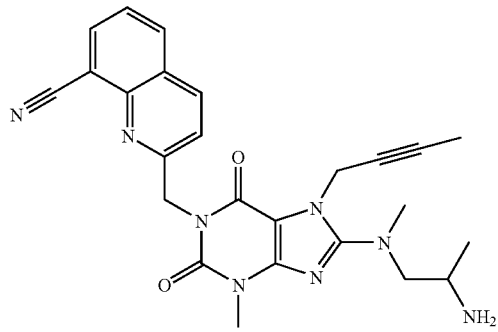 |
| (32) | 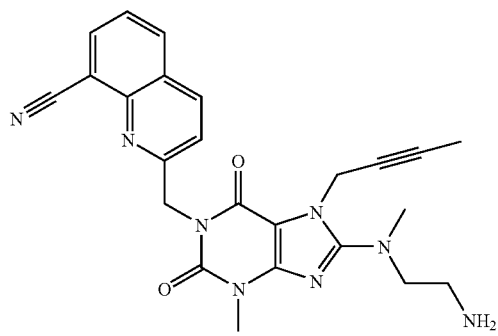 |
| (33) | 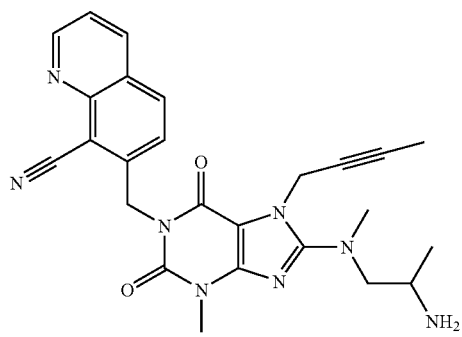 |
| (34) | 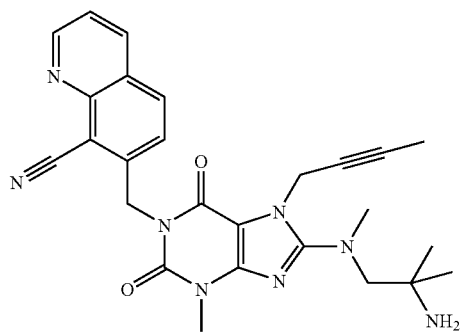 |
-continued
| Ex. | structure |
|---|---|
| (35) | 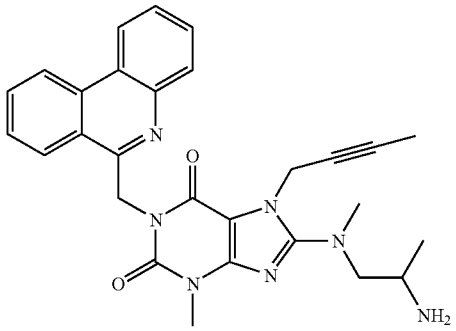 |
| (36) | 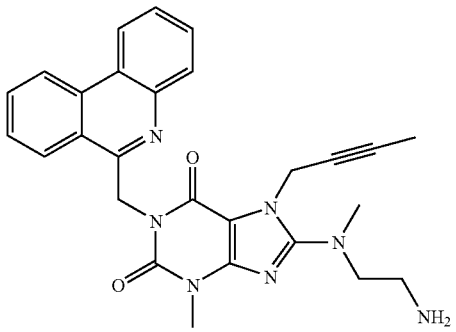 |
| (37) | 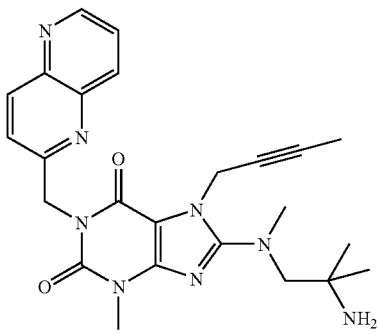 |
| (38) | 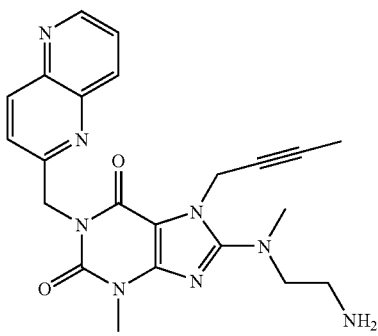 |

-continued
| Ex. | structure |
|---|---|
| (39) | 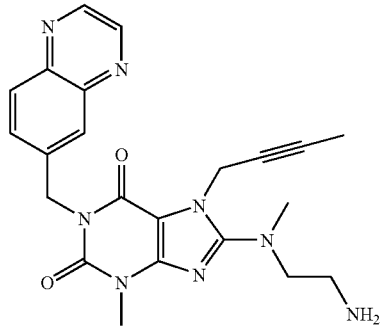 |
| (40) | 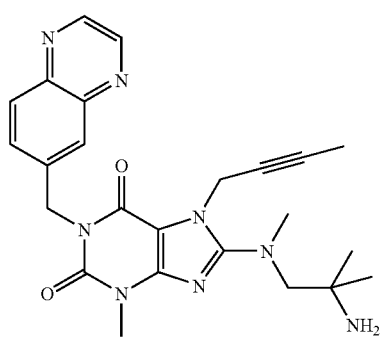 |
| (41) | 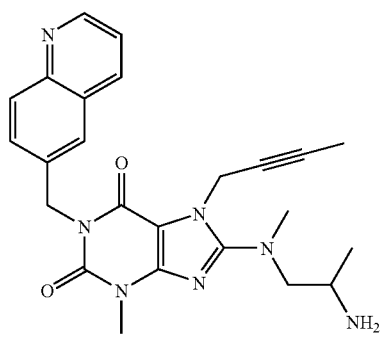 |
| (42) | 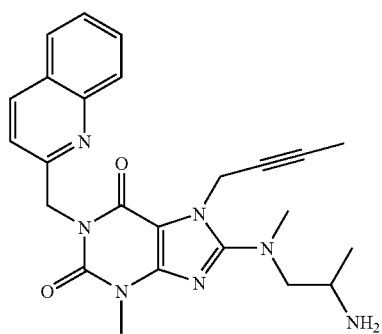 |
-continued
| Ex. | structure |
|---|---|
| (43) | 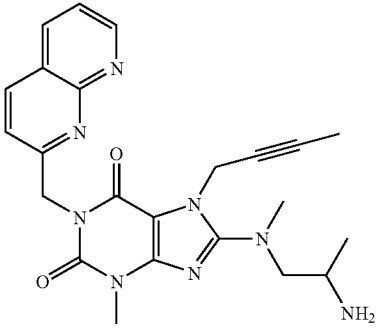 |
| (44) | 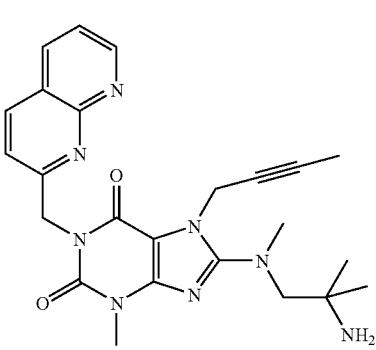 |
| (45) | 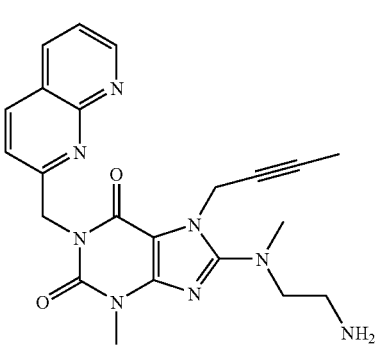 |
| (46) | 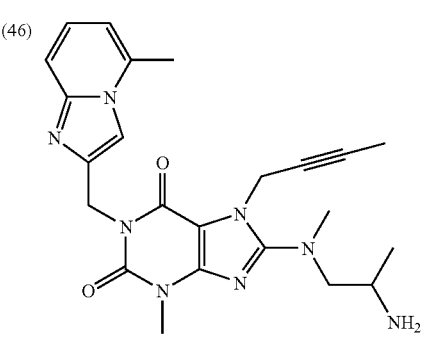 |

-continued
| Ex. | structure |
|---|---|
| (47) | 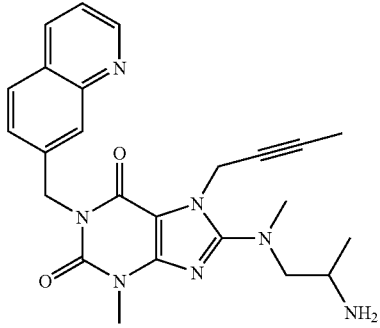 |
| (48) | 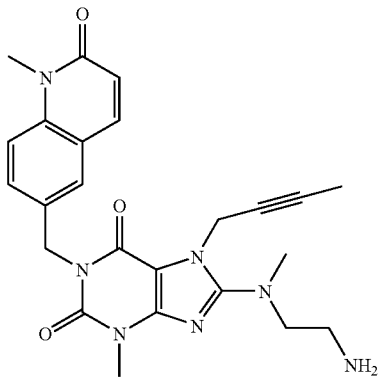 |
| (49) | 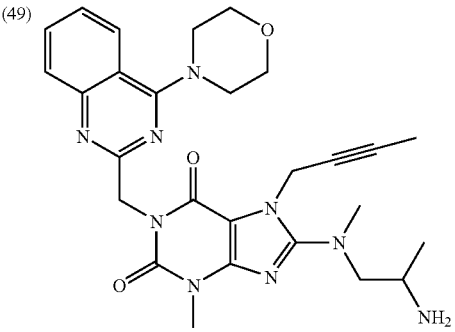 |
| (50) | 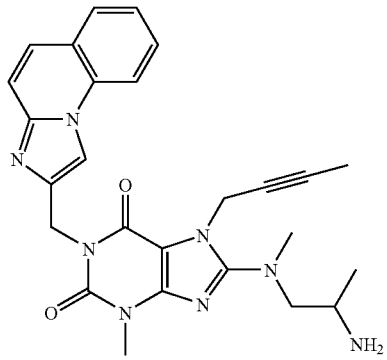 |
-continued
| Ex. | structure |
|---|---|
| (51) | 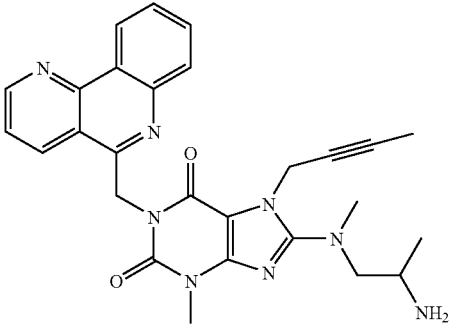 |
| (52) | 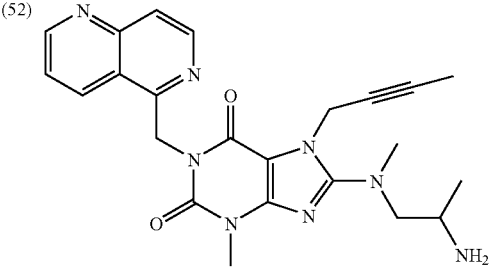 |
| (53) | 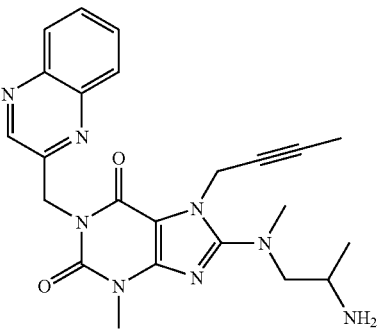 |
| (54) | 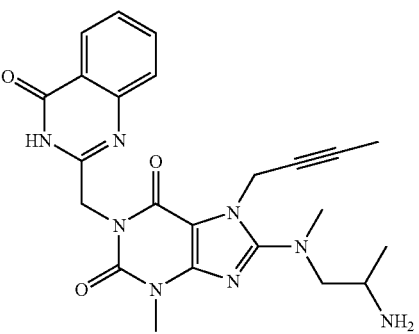 |

| Ex. | structure |
|---|---|
| (55) | 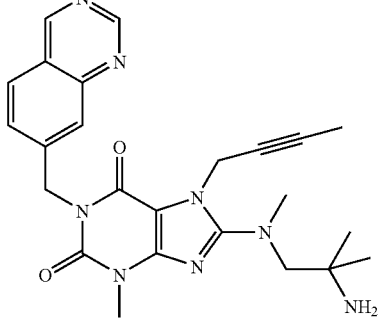 |
| (56) | 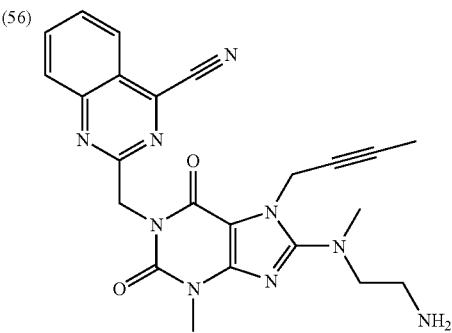 |
| (57) | 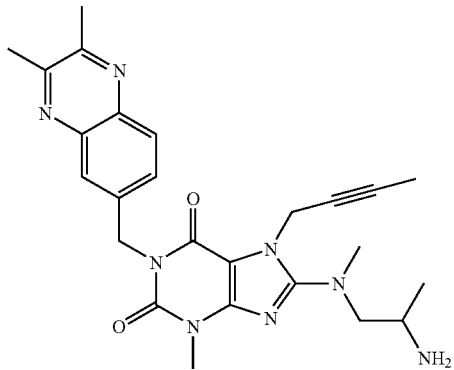 |
| Ex. | structure |
|---|---|
| (58) | 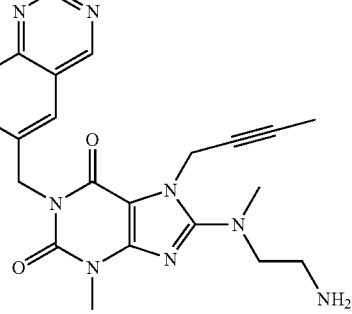 |
| (59) | 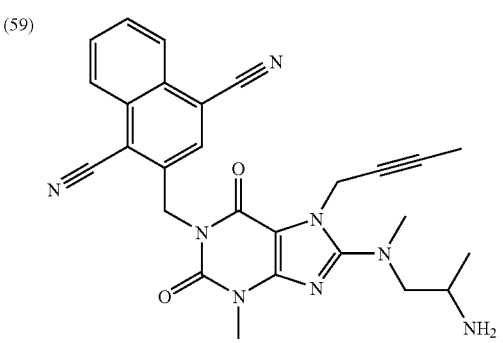 |
| (60) | 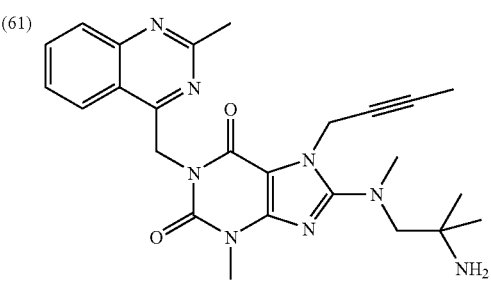 |
| (61) | |

| Ex. | structure |
|---|---|
| (62) | 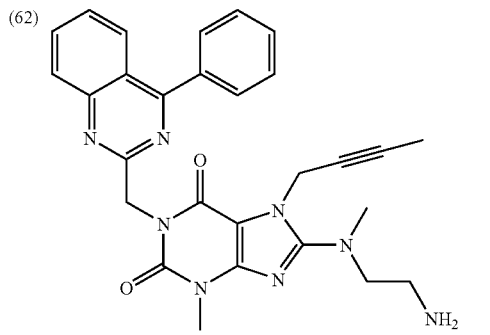 |
| (63) | 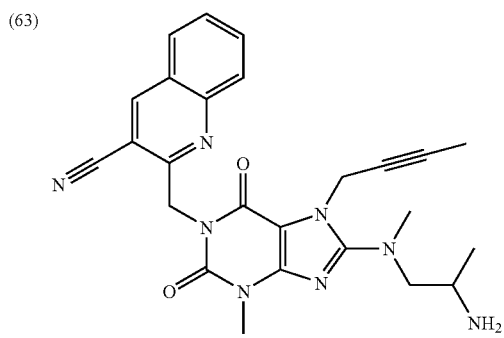 |
| (64) | 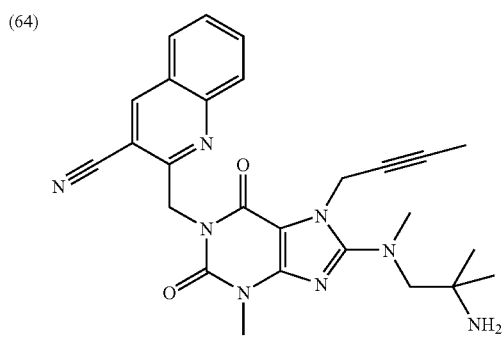 |
| (65) | 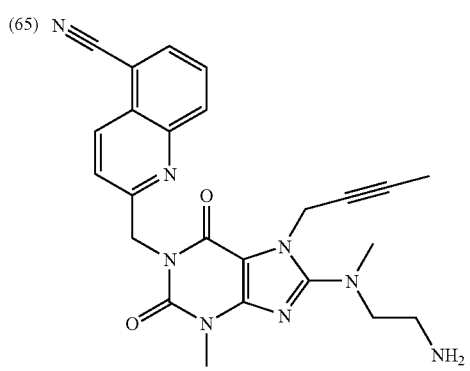 |
| (66) | 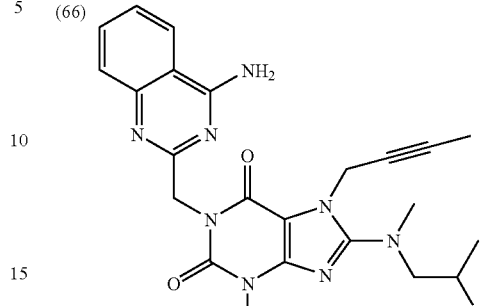 |
| (67) | 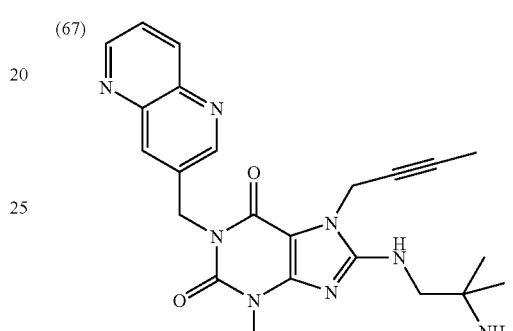 |
| (68) | 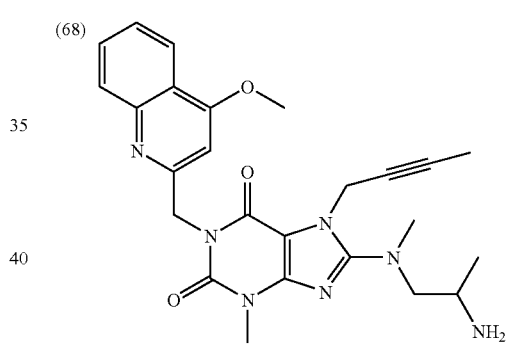 |

EXAMPLE 3

Coated Tablets Containing 75 mg of Active Substance 1 tablet core contains:

| | |
|---|---:|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl pyrrolidone, hydroxypropylmethylcellulose and half the specified amount of magnesium stearate.

Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 4

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 5

Tablets Containing 150 mg of Active Substance

Composition:

1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm.

The granules, dried at 45° C., are passed through the same screen again and mixed with the specified amount of magnesium stearate. Tablets are pressed from the mixture.

Weight of tablet: 300 mg
die: 10 mm, flat

EXAMPLE 6

Hard Gelatine Capsules Containing 150 mg of Active Substance 1 capsule contains:

| | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 7

Suppositories Containing 150 mg of Active Substance
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 8

Suspension Containing 50 mg of Active Substance
100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 9

Ampoules Containing 10 mg Active Substance
Composition:

| active substance | 10.0 mg |
|---|---|
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 10

Ampoules Containing 50 mg of Active Substance
Composition:

| active substance | 50.0 mg |
|---|---|
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. A compound of formula

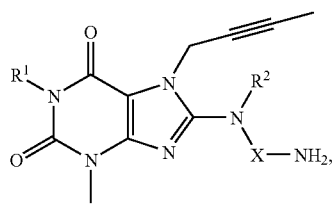

(I)

wherein
$R^1$ denotes an arylmethyl or arylethyl group,
a heteroarylmethyl or heteroarylethyl group,
an arylcarbonylmethyl group,
a heteroarylcarbonylmethyl group or
an arylprop-2—enyl or heteroarylprop-2–enyl group, wherein the propenyl chain may be substituted by 1 to 4 fluorine atoms or a cyano, $C_{1-3}$-alkyloxy-carbonyl or nitro group,
$R^2$ denotes a $C_{1-4}$-alkyl group, which may be straight-chain or branched, and X denotes a —$CH_2CH_2$— group, which may optionally be substituted by one or two $C_{1-3}$-alkyl groups, which may be identical or different,
while, unless otherwise stated, the above-mentioned alkyl, alkenyl and alkynyl groups may be straight-chain or branched, or a tautomer or salt thereof.

2. The compound according to claim 1, wherein $R^2$ denotes a methyl or ethyl group and X denotes a —$CH_2CH_2$— group, which may optionally be substituted by one or two methyl or ethyl groups, while the substituents may be identical or different, or a tautomer or salt thereof.

3. The compound according to claim 2, 1 wherein $R^1$ denotes a phenylmethyl, phenylcarbonylmethyl, phenylprop-2-enyl, pyridinylmethyl, pyrimidinylmethyl, naphthylmethyl, quinolinylmethyl, quinolinonylmethyl, imidazoquinolinylmethyl, isoquinolinylmethyl, quinazolinylmethyl, quinazolinonylmethyl, quinoxalinylmethyl, phenanthridinylmethyl, naphthyridinylmethyl, benzo- naphthiridinylmethyl, imidazopyridinylmethyl or benzotriazolylmethyl group which may be substituted in each case by one or two fluorine, chlorine, or bromine atoms or one or two cyano, nitro, amino, $C_{1-3}$-alkyl, $C_{1-3}$-alkyloxy, phenyl or morpholinyl groups, while the substituents are identical or different,
$R^2$ denotes a methyl group and
X denotes a —$CH_2CH_2$— group, which may optionally be substituted by one or two methyl groups, or
a tautomer or salt thereof.

4. The compound according to claim 3, wherein $R^1$ denotes a benzyl group substituted by one or two cyano groups or by a methoxy group and a cyano group or
$R^1$ denotes a pyridinylmethyl, pyrimidinylmethyl, quinolinylmethyl, isoquinolinylmethyl, quinazolinylmethyl, quinoxalinylmethyl, naphthyridinylmethyl or naphthylmethyl group, which may be substituted in each case by one or two cyano or methyl groups,
$R^2$ denotes a methyl group and
X denotes a —$CH(CH_3)$—$CH_2$— group, a —$CH_2$—$CH(CH_3)$— group or a —$CH_2$—$C(CH_3)_2$— group, or
a tautomer or salt thereof.

5. The compound according to claim 4, wherein
$R^1$ denotes a benzyl group substituted by a cyano group or a pyridinylmethyl, isoquinolinylmethyl, quinazolinylmethyl, quinoxalinylmethyl or naphthyridinylmethyl group, each of which may be substituted by a cyano or methyl group,
$R^2$ a methyl group and
X denotes a —$CH(CH_3)$—$CH_2$— group, a —$CH_2$—$CH(CH_3)$— group or a —$CH_2$—$C(CH_3)_2$— group, while in each case the carbon atom on the right is linked to the terminal amino group, or
a tautomer or salt thereof.

6. A compound selected from the group consisting of:
(a) 1-[(3-methyl-isoquinolin- 1 -yl)methyl]-3-methyl-7-(2-butyn- 1 -yl)-8-[(2-amino-ethyl) -methylamino]-xanthine,
(b) 1-[(4-methyl-quinazolin-2-yl)methyl]-3-methyl-7-(2-butyn-1-yl)-8[(2-amino-ethyl) -methylamino]-xanthine,
(c) 1-[(3-methyl-isoquinolin-1 -yl)methyl]-3-methyl-7(2-butyn-1-yl)-8-[(2-amino-2-methyl -propyl)-methylamino]-xanthine,
(d) 1-[(4-methyl-quinazolin-2-yl)methyl]-3-methyl-7-(2-butyn-1-yl)-8-[(2-amino-2-methyl -propyl)-methylamino]-xanthine,
(e) 1-[(3-methyl-isoquinolin-1-yl)methyl]-3-methyl-7-(2-butyn- 1-yl)-8-[(S)-(2-amino -propyl)-methylamino]-xanthine,
(f) 1-[(3-methyl-isoquinolin-1-yl)methyl]-3-methyl-7-(2-butyn- 1 -yl)-8-[(R)-(2-amino-propyl) -methylamino]-xanthine,
(g) 1-[(4-methyl-quinazolin-2-yl)methyl]-3-methyl-7-(2-butyn- 1-yl)-8-[(S)-(2-amino-propyl) -methylamino]-xanthine, (h) 1-[(4-methyl-quinazolin-2-yl)methyl]-3-methyl-7-(2-butyn- 1-yl)-8-[(R)-(2-amino-propyl) -methylamino]-xanthine, (i) 1-[(3-methyl-isoquinolin-1-yl)methyl]-3-methyl-7-(2-butyn-1-yl)-8-[(R)-(2-amino-1-methyl-ethyl)-methylamino]-]-xanthine, (j) 1-[(3-methyl-isoquinolin-1-yl)methyl]-3-methyl-7-(2-butyn-1-yl)-8-[(S)-(2-amino-1-methyl-ethyl)-methylamino]-]-xanthine, (k) 1-(2-cyano-benzyl)-3-methyl-7-(2-butyn-1-yl)-8-[(S)-(2-amino-propyl)-methyl-amino]-xanthine, (l) (1)-[([1,5]naphthyridin-2-yl)methyl]-3-methyl-7-(2-butyn-1-yl)- 8-[(S)-(2-amino-propyl)-methylamino]-xanthine, (m) 1-[(quinoxalin-6-yl)methyl]-3-methyl-7-(2-butyn-1-yl)- 8-[(S)-(2-amino-propyl ) -methylamino]-xanthine, (n) 1-[(3-cyano-pyridin-2-yl)methyl]-3-methyl-7-(2-butyn-1-yl)-8-[(S)-(2-amino-propyl -methylamino]-xanthine, (o) 1-[(4-cyano-isoquinolin-3-yl)methyl]-3-methyl-7-(2-butyn- 1-yl )-8-[(S)-(2-amino -propyl)-methylamino]-xanthine, (p) 1-(2-cyano-benzyl)-3-methyl-7-(2-butyn- 1-yl) 8- [(2-amino-2-methyl-propyl) -methylamino]-xanthine, and (q) 1-[(3-cyano-pyridin-2-yl)methyl]-3-methyl-7-(2-butyn- 1-yl)- 8-[(2-amino-2-methyl -propyl)-methylamino]-xanthine, or a salt thereof.

7. A physiologically acceptable salt of a compound according to claim 1 with an inorganic or organic acid or base.

8. A pharmaceutical composition comprising a pharmaceutically acceptable amount of a compound according to claim 1 together with one or more inert carriers or diluents.

9. A method of treating type II diabetes mellitus, or obesity, comprising administering to a patient in need thereof a therapeutically effective amount of a compound according to claim 1.

10. A method of treating type II diabetes mellitus comprising administering to a patient in need thereof a therapeutically effective amount of a compound according to claim 1.

11. A method of treating obesity comprising administering to a patient in need thereof a therapeutically effective amount of a compound according to claim 1.

12. The method of claim 9, wherein the compound is administered to the patient by intravenous route in an amount of 1 to 100 mg or by oral route in an amount of 1 to 1000 mg, in each case 1 to 4 times a day.

13. The method of claim 9, wherein the compound is administered to the patient by intravenous route in an amount of 1 to 30 mg, or by oral route in an amount of 1 to 100 mg, in each case 1 to 4 times a day.

\* \* \* \* \*